United States Patent
Devouassoux et al.

(10) Patent No.: US 10,214,338 B2
(45) Date of Patent: *Feb. 26, 2019

(54) PACKAGING SYSTEM FOR OXYGEN-SENSITIVE DRUGS

(71) Applicant: Fresenius Kabi Deutschland GmbH, Bad Homburg (DE)

(72) Inventors: Thomas Devouassoux, Saint Martin D-Heres (FR); Eric Forat, Lyons (FR); James Kenneth Proctor, Nashville, TN (US)

(73) Assignee: Fresenius Kabi Deutschland GmbH, Bad Homburg (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/375,784

(22) Filed: Dec. 12, 2016

(65) Prior Publication Data

US 2017/0088333 A1 Mar. 30, 2017

(51) Int. Cl.
*B65D 81/26* (2006.01)
*A61M 5/00* (2006.01)
(Continued)

(52) U.S. Cl.
CPC ............ *B65D 81/266* (2013.01); *A61B 50/30* (2016.02); *A61B 50/3001* (2016.02); *A61K 31/485* (2013.01); *A61K 31/5415* (2013.01); *A61M 5/002* (2013.01); *B65D 65/40* (2013.01); *B65D 75/36* (2013.01); *B65D 81/268* (2013.01); *A61B 2050/3005* (2016.02)

(58) Field of Classification Search
CPC ........ A61B 19/026; A61B 19/02; A61M 5/00; A61M 5/002; A61M 25/002; A61M 5/20; A61M 5/28; B65D 81/26; B65D 81/266; B65D 81/268; A61J 1/00; A61J 1/06; A61J 1/14
USPC ....... 604/23–26, 82–92, 134, 135, 181, 187, 604/200–207, 232–236; 206/204, 364, 206/438, 570–572
See application file for complete search history.

(56) References Cited

U.S. PATENT DOCUMENTS

| 1,048,712 A | 12/1912 | Lloyd |
| 2,715,627 A | 8/1955 | Mehltretter et al. |

(Continued)

FOREIGN PATENT DOCUMENTS

| CN | 1314789 A | 9/2001 |
| CN | 1607968 A | 4/2005 |

(Continued)

OTHER PUBLICATIONS

Feng-Sheng et al., "Compatibility and stability of Ketorolac Tromethamine and morphine hydrochloride in 0.9% sodium chloride injection," *The Pain Clinic*, 19(3):99-103 (2007).

(Continued)

*Primary Examiner* — Bryon Gehman
(74) *Attorney, Agent, or Firm* — Leydig, Voit & Mayer, Ltd.

(57) ABSTRACT

Described herein are pharmaceutical packaging systems which prevent oxidative degradation of oxygen-sensitive drugs, such systems including a primary packaging container with an oxygen permeable component, a secondary packaging with very low permeability to oxygen and an oxygen absorber.

21 Claims, 12 Drawing Sheets

Figure 1:
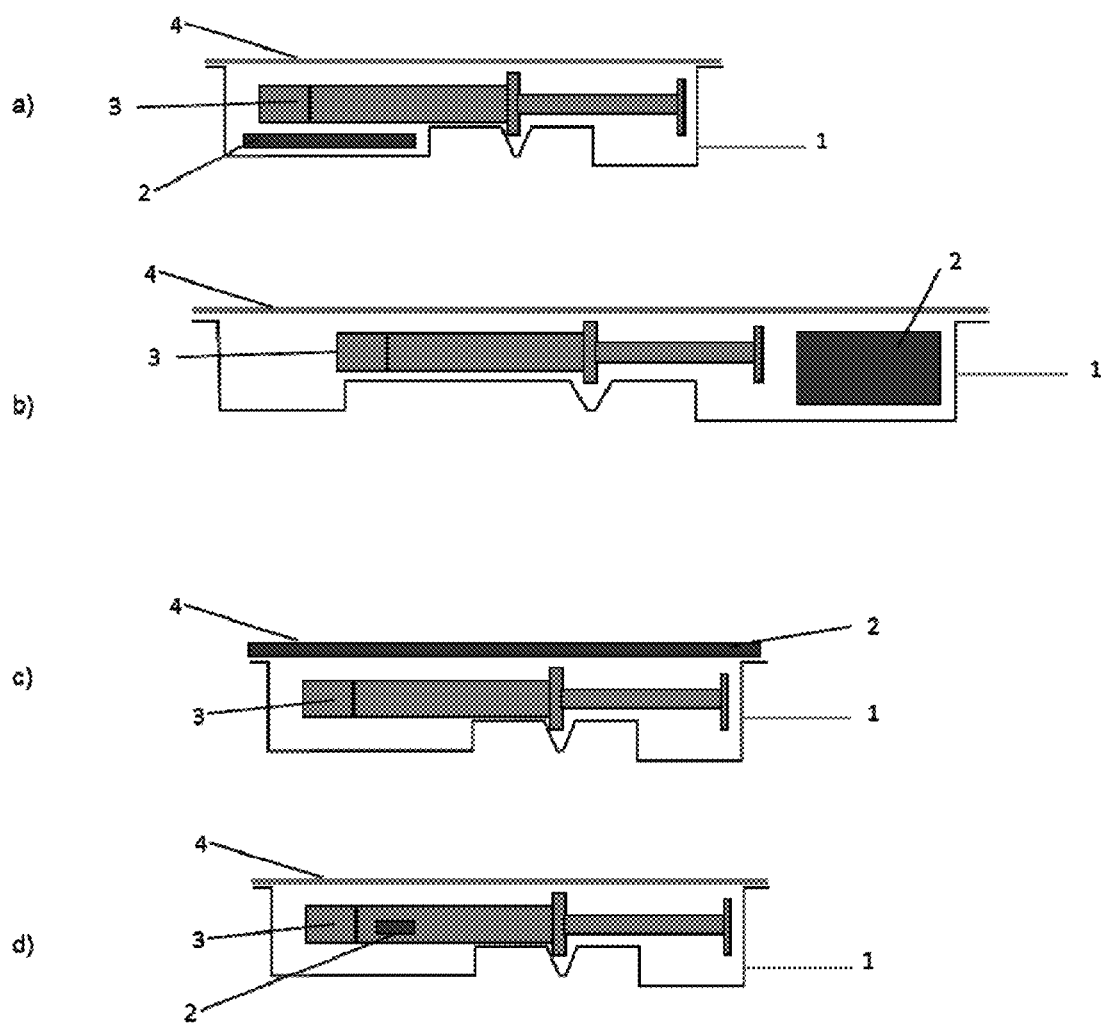

(51) Int. Cl.
  *A61B 50/30* (2016.01)
  *A61K 31/485* (2006.01)
  *A61K 31/5415* (2006.01)
  *B65D 65/40* (2006.01)
  *B65D 75/36* (2006.01)

(56) References Cited

U.S. PATENT DOCUMENTS

| | | |
|---|---|---|
| 4,071,620 A | 1/1978 | Sklar |
| 4,367,738 A | 1/1983 | Legendre et al. |
| 4,936,314 A | 6/1990 | Kasai et al. |
| 4,998,400 A | 3/1991 | Suzuki et al. |
| 5,030,216 A | 7/1991 | Theeuwes et al. |
| 5,295,965 A | 3/1994 | Wilmot |
| 5,346,697 A | 9/1994 | Tokuyama et al. |
| 5,449,745 A | 9/1995 | Sun et al. |
| 5,624,402 A | 4/1997 | Imbert |
| 5,650,485 A | 7/1997 | Sun et al. |
| 5,723,147 A | 3/1998 | Kim et al. |
| 5,807,572 A | 9/1998 | Kim et al. |
| 5,881,534 A | 3/1999 | Ahlqvist et al. |
| 5,891,467 A | 4/1999 | Willis |
| 5,931,809 A | 8/1999 | Gruber et al. |
| 5,962,016 A | 10/1999 | Willis |
| 5,997,899 A | 12/1999 | Ye et al. |
| 6,007,529 A | 12/1999 | Gustafsson et al. |
| 6,027,482 A | 2/2000 | Imbert |
| 6,054,584 A | 4/2000 | Ma et al. |
| 6,073,759 A | 6/2000 | Lamborne et al. |
| 6,171,613 B1 | 1/2001 | Ye et al. |
| 6,190,364 B1 | 2/2001 | Imbert |
| 6,193,998 B1 | 2/2001 | Ye et al. |
| 6,196,998 B1 | 3/2001 | Jansen et al. |
| 6,200,627 B1 | 3/2001 | Lubrecht |
| 6,217,550 B1 | 4/2001 | Capes |
| 6,241,999 B1 | 6/2001 | Ye et al. |
| 6,333,087 B1 | 12/2001 | Jerdee et al. |
| 6,406,644 B2 | 6/2002 | Jerdee et al. |
| 6,494,314 B1 | 12/2002 | Lamborne et al. |
| 6,569,506 B1 | 5/2003 | Jerdee et al. |
| 6,688,468 B2 | 2/2004 | Waterman |
| 6,743,216 B2 | 6/2004 | Odell et al. |
| 6,866,142 B2 | 3/2005 | Lamborne et al. |
| 6,875,400 B2 | 4/2005 | Speer et al. |
| 7,000,770 B2 | 2/2006 | Clarke et al. |
| 7,137,968 B1 | 11/2006 | Burrell et al. |
| 7,141,042 B2 | 11/2006 | Lubrecht |
| 7,708,719 B2 | 5/2010 | Wilmot et al. |
| 7,794,804 B2 | 9/2010 | Jerdee et al. |
| 7,938,580 B2 | 5/2011 | Gaskell et al. |
| 7,998,120 B2 | 8/2011 | Sano et al. |
| 8,002,737 B2 | 8/2011 | Tennican |
| 8,075,535 B2 | 12/2011 | Carrel et al. |
| 8,552,025 B2 | 10/2013 | Sanghvi et al. |
| 8,652,094 B2 | 2/2014 | David et al. |
| 8,679,068 B2 | 3/2014 | Young |
| 9,072,781 B2 | 7/2015 | Cuine et al. |
| 9,095,324 B2 * | 8/2015 | Peck .................... A61B 19/026 |
| 9,192,608 B2 | 11/2015 | Cuine et al. |
| 9,248,229 B2 | 2/2016 | Devouassoux et al. |
| 9,545,473 B2 | 1/2017 | Devouassoux et al. |
| 2001/0023025 A1 | 9/2001 | Jerdee et al. |
| 2002/0132359 A1 | 9/2002 | Waterman |
| 2002/0153511 A1 | 10/2002 | Cotterman et al. |
| 2003/0034264 A1 | 2/2003 | Hamai et al. |
| 2003/0042166 A1 | 3/2003 | Waterman |
| 2003/0106824 A1 | 6/2003 | Wilmot et al. |
| 2003/0152727 A1 | 8/2003 | Jerdee et al. |
| 2004/0187438 A1 | 9/2004 | Clarke et al. |
| 2004/0220545 A1 | 11/2004 | Heruth et al. |
| 2004/0243214 A1 | 12/2004 | Farrell et al. |
| 2004/0266806 A1 | 12/2004 | Sanghvi et al. |
| 2004/0267194 A1 | 12/2004 | Sano et al. |
| 2006/0032768 A1 | 2/2006 | Hamai et al. |
| 2006/0229583 A1 | 10/2006 | Nagao et al. |
| 2006/0260967 A1 | 11/2006 | Clarke et al. |
| 2007/0163917 A1 | 7/2007 | Friesen et al. |
| 2008/0070975 A1 | 3/2008 | Shah et al. |
| 2008/0072992 A1 | 3/2008 | Baleriaux et al. |
| 2008/0249247 A1 | 10/2008 | Shang et al. |
| 2009/0032426 A1 | 2/2009 | Tateishi et al. |
| 2009/0246257 A1 | 10/2009 | Modi |
| 2009/0281504 A1 | 11/2009 | Nanba et al. |
| 2010/0032686 A1 | 2/2010 | Ishll et al. |
| 2010/0174268 A1 | 7/2010 | Wilmot et al. |
| 2010/0261744 A1 | 10/2010 | Sanghvi et al. |
| 2010/0261745 A1 | 10/2010 | Sanghvi et al. |
| 2010/0261746 A1 | 10/2010 | Sanghvi et al. |
| 2010/0267758 A1 | 10/2010 | Sanghvi et al. |
| 2010/0326868 A1 | 12/2010 | McClain et al. |
| 2011/0020451 A1 | 1/2011 | Bartholomaeus et al. |
| 2011/0130717 A1 | 6/2011 | David et al. |
| 2011/0136847 A1 | 6/2011 | Chan et al. |
| 2012/0143144 A1 | 6/2012 | Young |
| 2013/0081974 A1 | 4/2013 | Hilliard et al. |
| 2014/0262883 A1 | 9/2014 | Devouassoux et al. |
| 2014/0275144 A1 | 9/2014 | Cuine et al. |
| 2015/0246036 A1 | 9/2015 | Cuine et al. |
| 2016/0175297 A1 | 6/2016 | Cuine et al. |

FOREIGN PATENT DOCUMENTS

| | | |
|---|---|---|
| CN | 1767831 A | 5/2006 |
| EP | 0 622 072 A2 | 11/1994 |
| EP | 0 673 261 A1 | 9/1995 |
| EP | 0 837 069 A1 | 4/1998 |
| EP | 0 882 441 A2 | 12/1998 |
| EP | 0 909 555 A1 | 4/1999 |
| EP | 1 241 110 A1 | 9/2002 |
| EP | 1 243 524 A2 | 9/2002 |
| EP | 0 909 555 B1 | 5/2004 |
| EP | 1 557 367 A1 | 7/2005 |
| EP | 1 586 347 A1 | 10/2005 |
| EP | 1 616 549 A1 | 1/2006 |
| EP | 1 653 930 B1 | 12/2007 |
| EP | 1 875 889 A1 | 1/2008 |
| EP | 1 827 283 B1 | 2/2009 |
| EP | 2 080 501 A1 | 7/2009 |
| EP | 2 968 132 A1 | 1/2016 |
| EP | 2 968 729 A1 | 1/2016 |
| GB | 2 471 726 A | 1/2011 |
| JP | S56-125876 U | 9/1981 |
| JP | S63-11160 A | 1/1988 |
| JP | 2002-253641 A | 9/2002 |
| JP | 2004-057321 A | 2/2004 |
| JP | 2005-508231 A | 3/2005 |
| JP | 2006-016053 A | 1/2006 |
| JP | 2008/067989 A | 3/2008 |
| JP | 2009-154925 A | 7/2009 |
| JP | 2010-162344 A | 7/2010 |
| JP | 2011-005182 A | 1/2011 |
| JP | 2012-532638 A | 12/2012 |
| WO | WO 94/13328 A1 | 6/1994 |
| WO | WO 98/00159 A1 | 1/1998 |
| WO | WO 98/26819 A1 | 6/1998 |
| WO | WO 99/22691 A1 | 5/1999 |
| WO | WO 00/76507 A1 | 12/2000 |
| WO | WO 03/039632 A2 | 5/2003 |
| WO | WO 2004/091623 A1 | 10/2004 |
| WO | WO 2007/022609 A1 | 3/2007 |
| WO | WO 2011/004137 A1 | 1/2011 |
| WO | WO 2014/140095 A1 | 9/2014 |
| WO | WO 2014/140097 A1 | 9/2014 |

OTHER PUBLICATIONS

Fine et al., "Establishing "Best practices" for opioid rotation: Conclusions of an expert panel," *J Pain and Symptom Manage* 38(3):418-425 (2009).

Hospira Morphine Label EN-1179, pp. 1-8 (2006).

Morphin Merck Tropfen. Bundesverband der Pharmazeutischen Industrie: "Rote Liste 2002", Rote Liste Service GmbH (2002).

(56) References Cited

OTHER PUBLICATIONS

European Patent Office, International Search Report in International Application No. PCT/EP2014/054834 (dated Jun. 4, 2014).
European Patent Office, Written Opinion in International Application No. PCT/EP2014/054834 (dated Jun. 4, 2014).
European Patent Office, International Search Report in International Application No. PCT/EP2014/054831 (dated May 6, 2014).
European Patent Office, Written Opinion in International Application No. PCT/EP2014/054831 (dated May 6, 2014).
Balls, "Concerning Pseudomorphine," *J. Biol. Chem.* 71: 537-542 (1927).
Morphine Sulfate Injection USP, Preservative Free, Solution for Intravenous Use, CII, Hospira, *Highlights of Prescribing Information*, U.S. Food and Drug Administration, Reference ID 3043802 (2011)—15 pgs. www.accessdata.fda.gov/drugsatfda_docs/label/2011/202515s000lbl.pdf.
Morphine Sulfate Oral Solution and Morphine Sulfate Tablets, CII, Roxane Laboratories, *Highlights of Prescribing Information*, U.S. Food and Drug Administration (2008)—14 pgs. www.accessdata.fda.gov/drugsatfda_docs/label/2008/022195.022207lbl.pdf.
Morphine Sulfate Oral Solution, CII, Lannett Company, *Highlights of Prescribing Information*, U.S. Food and Drug Administration, Reference ID 2965365 (2011)—19 pgs. www.accessdata.fda.gov/drugsatfda_docs/label/2011/201517s000lbl.pdf.
Pan, "Industrial Pharmacy," p. 215 (2010).
Preechagoon et al., "Formulation Development and Stability Testing of Oral Morphine Solution Utilizing Preformulation Approach," *J. Pharm Pharmaceut Sci* 8(2): 362-369 (2005).
Preservation-Free Morphine Sulfate Injection, USP, Hospira EN-0597, 2004 (7 pgs.) https://www.pfizerinjectables.com/sites/default/files/prod/child/uspi/EN-0597_1.pdf.
Vermeire et al., "Stability and compatibility of morphine," *International Journal of Pharmaceutics* 187: 17-51 (1999).
Yeh et al., "Stability of Morphine in Aqueous Solution III—Kinetics of Morphine Degradation in Aqueous Solution," *J Pharm Sci.* 50: 35-42 (1961).
State Intellectual Property Office of the People's Republic of China, First Notification of Office Action in Chinese Patent Application No. 201410097880.9 (dated Jun. 23, 2016).
European Patent Office, Communication pursuant to Article 94(3) EPC in European Patent Application No. 14709937.8 (dated Oct. 6, 2016).
State Intellectual Property Office of the People's Republic of China, Second Notification of Office Action in Chinese Patent Application No. 201410097880.9 (dated Feb. 23, 2017).
Japan Patent Office, Notice of Reasons for Refusal in Japanese Patent Application No. 562123/2015 (Jun. 6, 2017).
IP Australia, Examination report No. 1 in Australian Patent Application No. 2014230836 (Aug. 22, 2017).
State Intellectual Property Office of the People'S Republic of China, Third Notification of Office Action in Chinese Patent Application No. 201410097880.9 (Aug. 23, 2017).
European Patent Office, Communication pursuant to Article 94(3) EPC in European Patent Application No. 14709937.8 (Jun. 22, 2017).
State Intellectual Property Office of the People'S Republic of China, Fourth Notification of Office Action in Chinese Patent Application No. 201410097880.9 (Dec. 28, 2017).
Japan Patent Office, Notice of Reasons for Refusal in Japanese Patent Application No. 562123/2015 (Jan. 23, 2018).
State Intellectual Property Office of the People's Republic of China, Notification to Grant Patent Right for Invention in Chinese Patent Application No. 201410097880.9 (May 11, 2018).

* cited by examiner

PACKAGING SYSTEM FOR OXYGEN-SENSITIVE DRUGS

CROSS-REFERENCE TO RELATED APPLICATIONS

This patent application is a continuation of U.S. patent application Ser. No. 14/968,351, filed Dec. 14, 2015, which is a continuation of U.S. patent application Ser. No. 14/207,207, filed Mar. 12, 2014, now U.S. Pat. No. 9,248,229, and which claims the benefit of U.S. Provisional Application No. 61/785,158, filed Mar. 14, 2013, which are each incorporated herein by reference in their entireties.

BACKGROUND OF THE INVENTION

Oxygen sensitivity in drugs and their formulations is a large concern in pharmaceutical development. Often, the oxygen sensitive drug or formulation requires additional excipients, packaging and/or manufacturing steps for stability enhancement and degradation prevention. Chemical approaches, such as pH control, addition of an antioxidant, and control of components are usually considered first as a means of enhancing stability of oxygen-sensitive solutions. A downside of chemical approaches is added complexity to the formulation and additional research needed for identity, compatibility and toxicity of suitable excipients. Nitrogen gassing of a solution and nitrogen blanketing of a container during and/or after filling of a drug is also commonly used in the pharmaceutical industry. However, the efficiency of this process is limited and leads to a residual oxygen level of a few percent. With this standard manufacturing and filling process, the shelf life of oxygen sensitive products is generally reduced to typically around six months as compared to drugs that are not sensitive to oxygen.

BRIEF SUMMARY OF THE INVENTION

Provided herein are pharmaceutical packaging system for an injectable oxygen-sensitive drug. In one aspect, the pharmaceutical packaging system comprises a primary packaging container comprising an oxygen-sensitive drug, wherein the primary packaging container has an oxygen permeable component and wherein the primary packaging container is packaged under inert conditions, a hermetically sealed secondary packaging which envelops the primary packaging container, wherein the secondary packaging has very low permeability to oxygen, and an oxygen absorber, wherein the oxygen absorber removes the oxygen present at the time of packaging assembly at a rate of up to 60%, up to 70%, up to 80%, up to 90%, or up to 100% per day in the secondary packaging and up to 60%, up to 70%, up to 80%, up to 90%, or up to 100% per month in the primary packaging container.

In some embodiments of the pharmaceutical packaging system, the primary packaging container is a syringe, cartridge, vial or drug storage container. In certain instances, the primary packaging container is a syringe. In some embodiments, the primary packaging container is plastic or glass. In certain instances, the primary packaging container is glass. In some embodiments, the oxygen permeable component is an oxygen permeable cap. In some embodiments, the oxygen permeable component is rubber or plastic. In some embodiments, the oxygen permeable component is a rubber cap.

In some embodiments of pharmaceutical packaging system, the secondary packaging is a bag or blister packaging. In some embodiments, the secondary packaging comprises an oxygen barrier material selected from the group consisting of high density polyethylene (HDPE), ethylene/vinyl alcohol copolymer (EVOH), polypropylene (PP), polyethylene terephthalate (PET), polyethylene naphthalate (PEN), and polyamide (PA), metalized film, aluminum foil, oxide coated films and combinations thereof. In certain instances, the oxygen barrier material is EVOH. In some embodiments, the secondary packaging material comprises a top and bottom web. In certain instances, the bottom web is a thermoformed blister. In certain instances, the thermoformed blister comprises EVOH. In certain instances, the top web is aluminum foil or an EVOH layer.

In some embodiments of pharmaceutical packaging system, the oxygen absorber is placed inside the secondary packaging. In certain instances, the oxygen absorber is a sachet, pouch, canister, capsule, label, sticker, strip, patch, cartridge or container. In some embodiments, the oxygen absorber is incorporated into the material of the secondary packaging. In some embodiments, the oxygen absorber is a coating or layer that lines the secondary packaging. In some embodiments, the oxygen absorber is selected from the group consisting of reduced iron compounds, catechol, ascorbic acid and analogs thereof, metal ligands, unsaturated hydrocarbons and polyamides. In certain instances, the oxygen absorber is a reduced iron compound.

In some embodiments of pharmaceutical packaging system, the oxygen absorber reduces the oxygen level from the time of packaging assembly to about zero percent in about one to seven days, or one to three days in the secondary packaging and in about one to six months, or one to three months in the primary packaging container. In some embodiments, oxygen absorber reduces the oxygen level from the time of packaging assembly to about zero percent in about one day in the secondary packaging and in about one month in the primary packaging container. In some embodiments, the oxygen levels in the primary and secondary packaging remain at about zero percent after the initial reduction in the primary and secondary packaging for at least one year. In some embodiments, the oxygen levels in the primary and secondary packaging remain at about zero percent after the initial reduction in the primary and secondary packaging for at least three years.

In some embodiments of pharmaceutical packaging system, the oxygen-sensitive drug is selected from the group consisting of morphine, hydromorphone, promethazine, dopamine, epinephrine, norepinephrine, esterified estrogen, ephedrine, pseudoephedrine, acetaminophen, ibuprofen, danofloxacin, erythromycin, penicillin, cyclosporine, methyldopate, cetirizine, diltiazem, verapamil, mexiletine, chlorothiazide, carbamazepine, selegiline, oxybutynin, vitamin A, vitamin B, vitamin C, L-cysteine and L-tryptophan. In certain instances, the oxygen-sensitive drug is morphine. In certain instances, the oxygen-sensitive drug is hydromorphone. In certain instances, the oxygen-sensitive drug is promethazine.

In another aspect, the pharmaceutical packaging system comprises a primary packaging container comprising an oxygen-sensitive drug, wherein the primary packaging container has an oxygen permeable component and wherein the primary packaging container is packaged under inert conditions, a hermetically sealed secondary packaging which envelops the primary packaging container, wherein the secondary packaging has very low permeability to oxygen, and an oxygen absorber, wherein the oxygen absorber, after removal of the oxygen present at the time of packaging assembly, maintains an oxygen level of about zero percent in the secondary packaging and an oxygen level of about zero percent in the primary packaging container for about one year. In some embodiments, the oxygen levels in the primary and secondary packaging remain at about zero percent after the initial reduction in the primary and secondary packaging for at least one year. In some embodiments, the oxygen levels in the primary and secondary packaging remain at about zero percent after the initial reduction in the primary and secondary packaging for at least three years.

Also provided herein is a pharmaceutical packaging system for an injectable oxygen-sensitive drug, the packaging system comprising a syringe filled under inert conditions with an injectable oxygen-sensitive drug, wherein the syringe has an oxygen permeable tip cap, a hermetically sealed blister packaging which houses the syringe, wherein the blister packaging comprises a multilayer bottom web and a multilayer top web lid; and an oxygen absorber, wherein the oxygen absorber reduces the oxygen level present from the time of packaging assembly to about zero percent in about one to three days in the blister packaging and in about one to three months in the syringe.

In some embodiments, the syringe is plastic or glass. In some embodiments, the secondary packaging material is a thermoformed, aluminum-based cold formed, or molded blister. In some embodiments, the multilayer bottom web comprises ethylene/vinyl alcohol copolymer (EVOH). In some embodiments, the top web lid comprises aluminum foil or EVOH.

In some embodiments, oxygen absorber is placed inside the blister packaging. In certain instances, oxygen absorber is a canister. In some embodiments, the oxygen absorber has a capacity to absorb about 30 cc oxygen at 1 atm. In some embodiments, the oxygen absorber is iron-based. In some embodiments, the oxygen absorber reduces the oxygen level in the blister packaging from the time of packaging assembly to about zero percent at about one day. In some embodiments, the oxygen absorber reduces the oxygen level in the syringe from the time of packaging assembly to about zero percent at about one month. In some embodiments, the oxygen level remains at about zero percent in the syringe and the blister packaging for at least three years.

In some embodiments, the injectable oxygen-sensitive drug is morphine. In some embodiments, the injectable oxygen-sensitive drug is hydromorphone. In some embodiments, the injectable oxygen-sensitive drug is promethazine.

Also provided herein is a pharmaceutical packaging system for injectable morphine, the packaging system comprising a syringe filled under inert conditions with morphine, wherein the syringe has an oxygen permeable tip cap, a hermetically sealed blister packaging which houses the syringe, wherein the blister packaging comprises a multilayer bottom web and a multilayer top web lid; and an oxygen absorber, wherein the oxygen absorber reduces the oxygen level from the time of packaging assembly to about zero percent in about one to three days in the blister packaging and in about one to three months in the syringe.

BRIEF DESCRIPTION OF THE DRAWING(S)

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings:

FIG. 1: Schematic of exemplary packaging system embodiments with oxygen absorber in a sachet (a), in the lid (b), in a canister (c) and positioned on the primary packaging (d).

Figure 2:
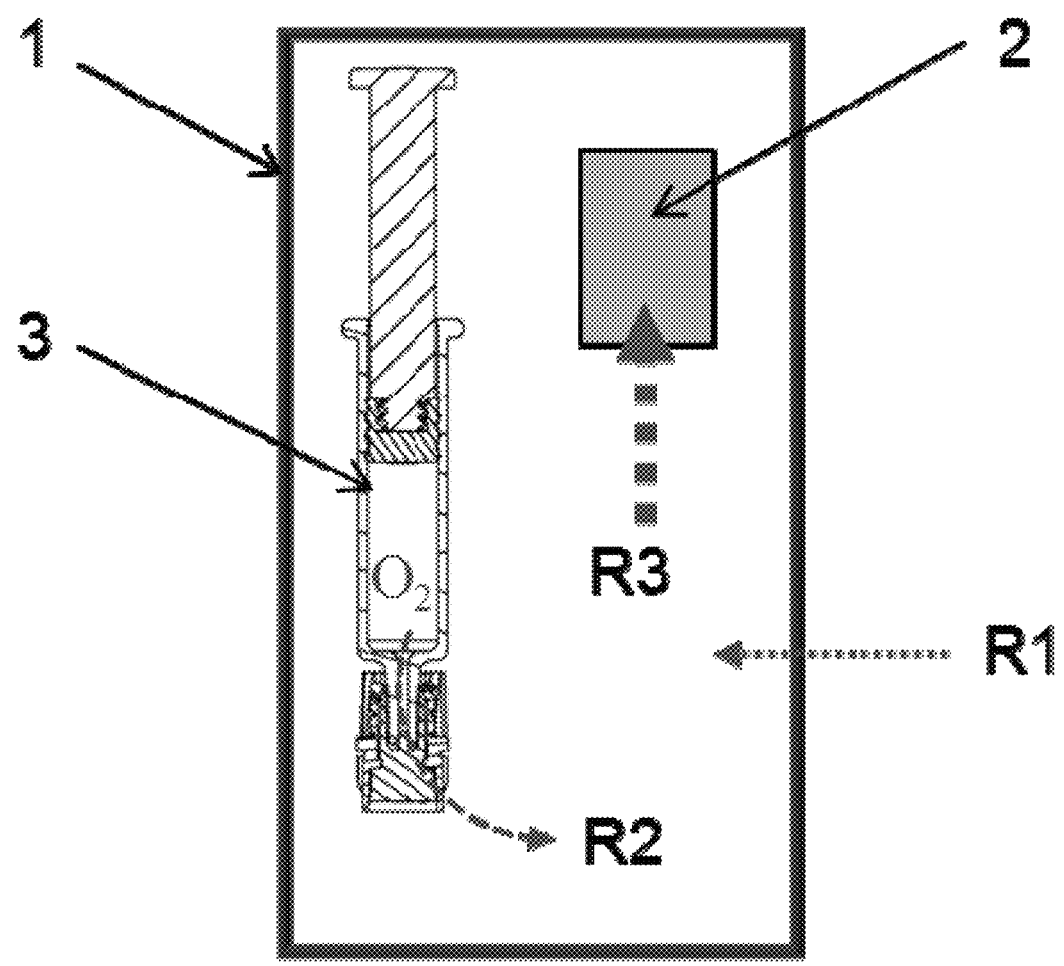

FIG. 2: Schematic depicting a packaging system having (1) oxygen barrier secondary packaging, (2) oxygen absorber, and (3) primary packaging (syringe) along with oxygen transfer rates of the various environments.

Figure 3:
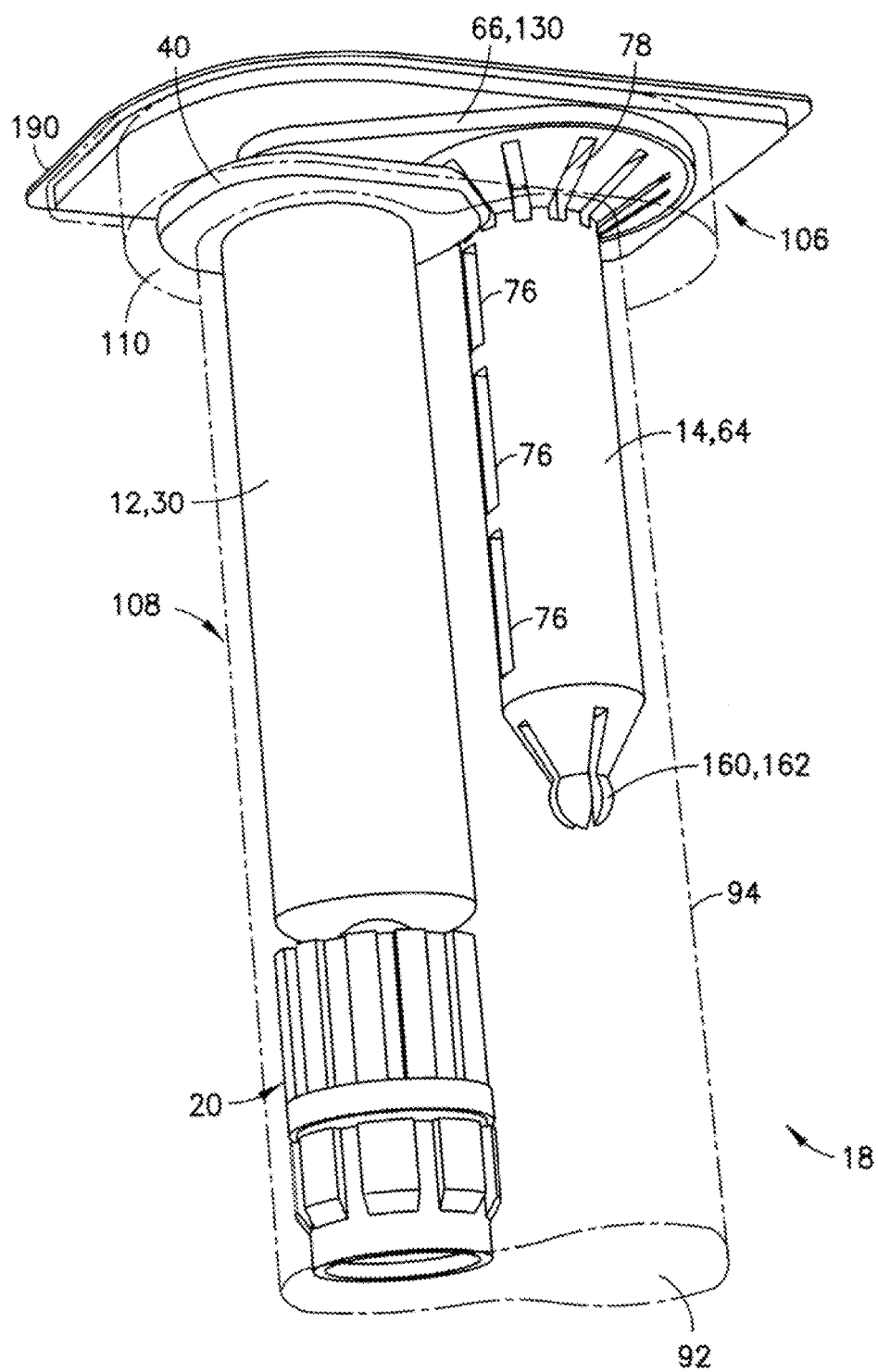

FIG. 3: Drawing of an exemplary syringe and secondary packaging embodiment where a secondary packaging includes a first compartment to receive a syringe barrel and second compartment to receive a plunger rod separate and detached from the syringe barrel.

Figure 4:
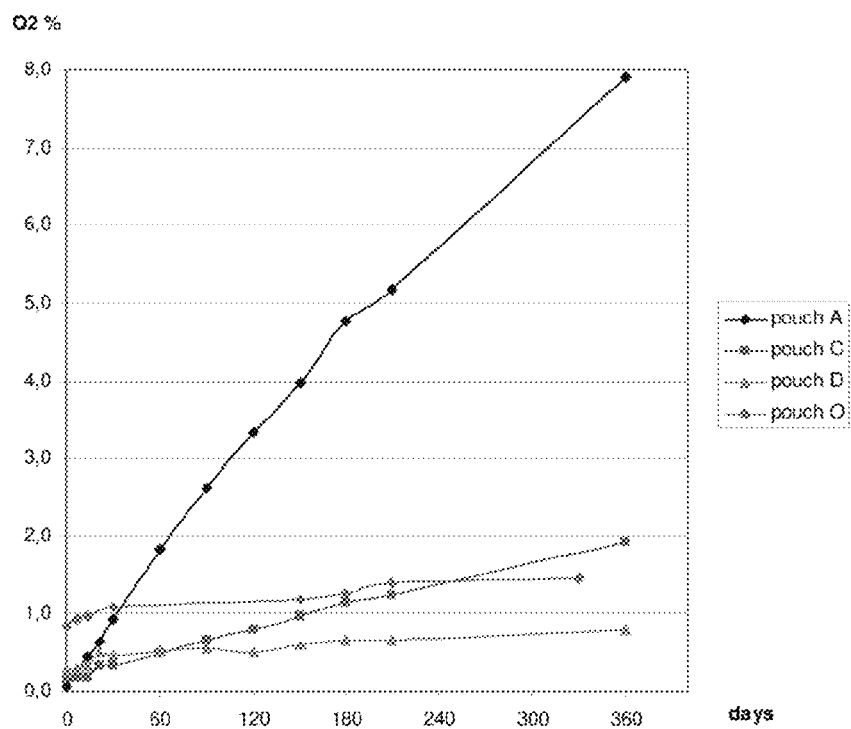

FIG. 4: Oxygen levels in pouch environments for packaging configurations A, C, D and O stored at 25° C./60% Relative Humidity (RH).

Figure 5:
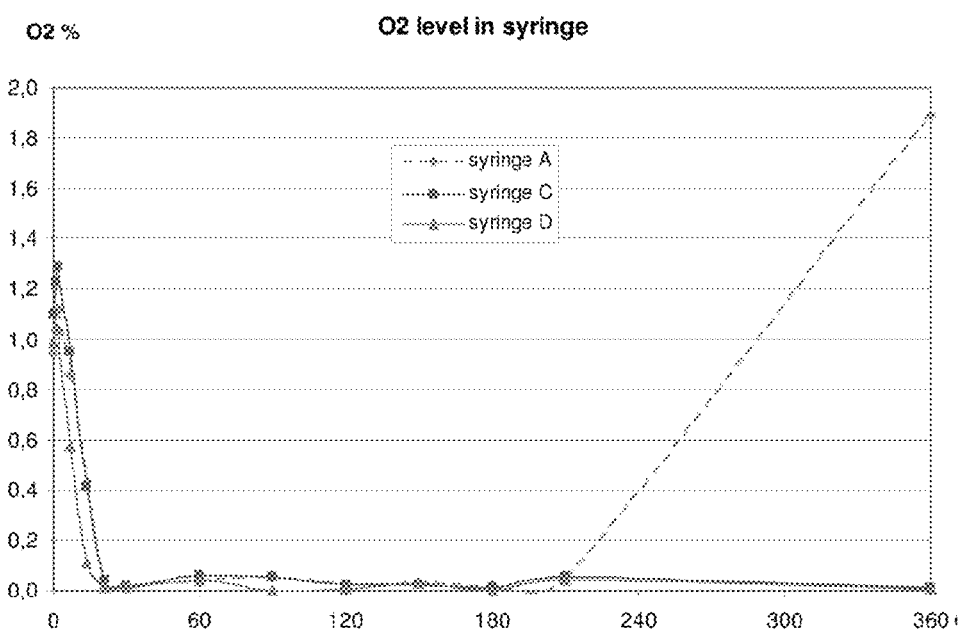

FIG. 5: Oxygen levels in syringe barrels for packaging configurations A, C and D stored at 25° C./60% RH.

Figure 6:
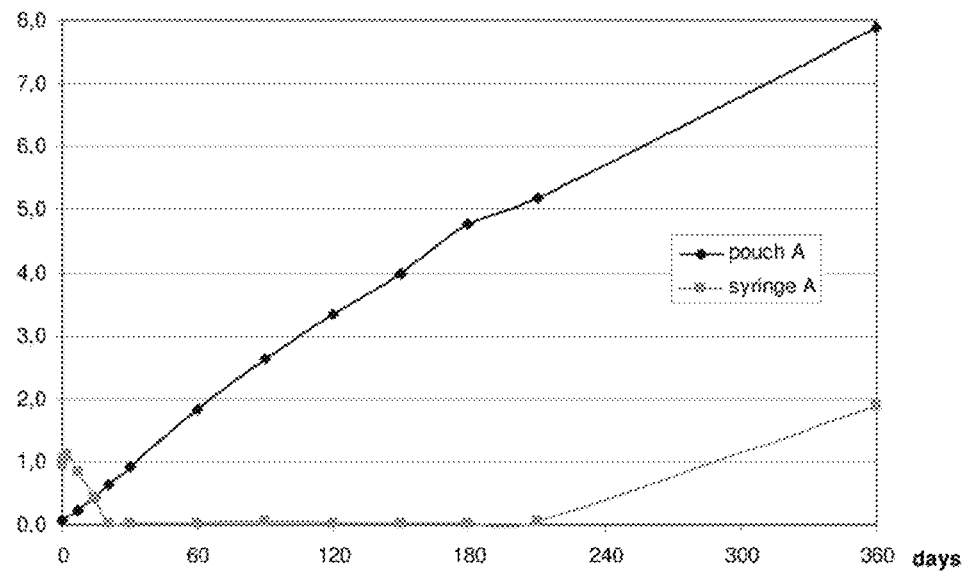

FIG. 6: Comparison of oxygen levels in syringe barrels versus pouch environments for packaging configuration A stored at 25° C./60% RH.

Figure 7:
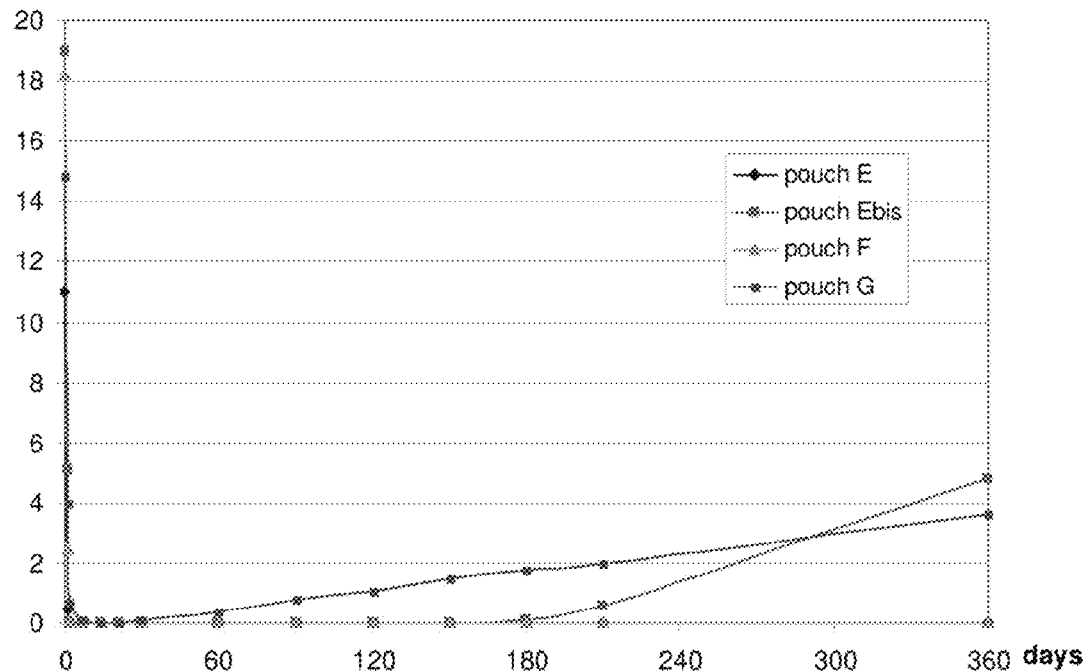

FIG. 7: Oxygen levels in pouch environments for packaging configurations E, E bis, F and G stored at 25° C./60% RH.

Figure 8:
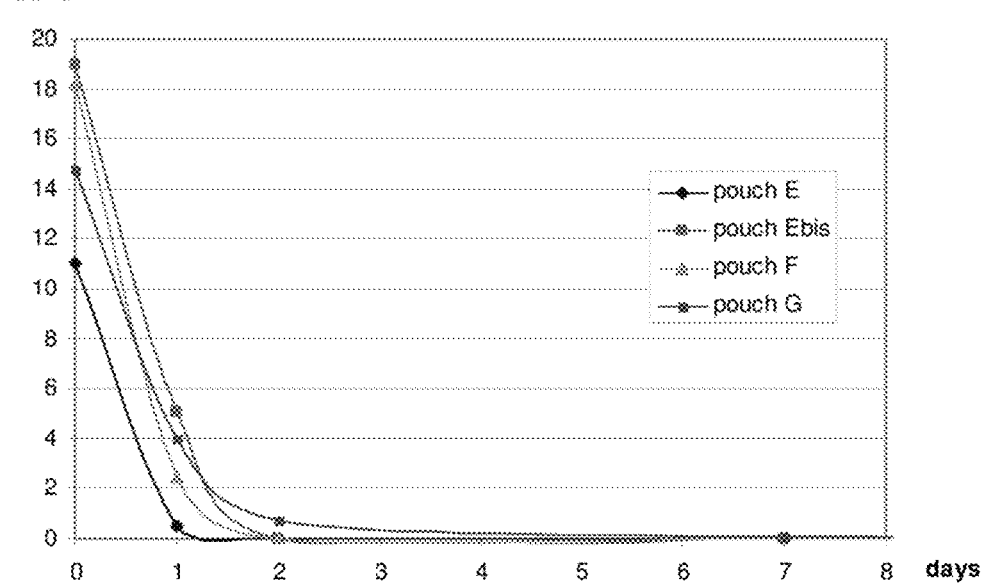

FIG. 8: Oxygen levels in pouch environments for packaging configurations E, E bis, F and G stored at 25° C./60% RH for the first 8 days.

Figure 9:
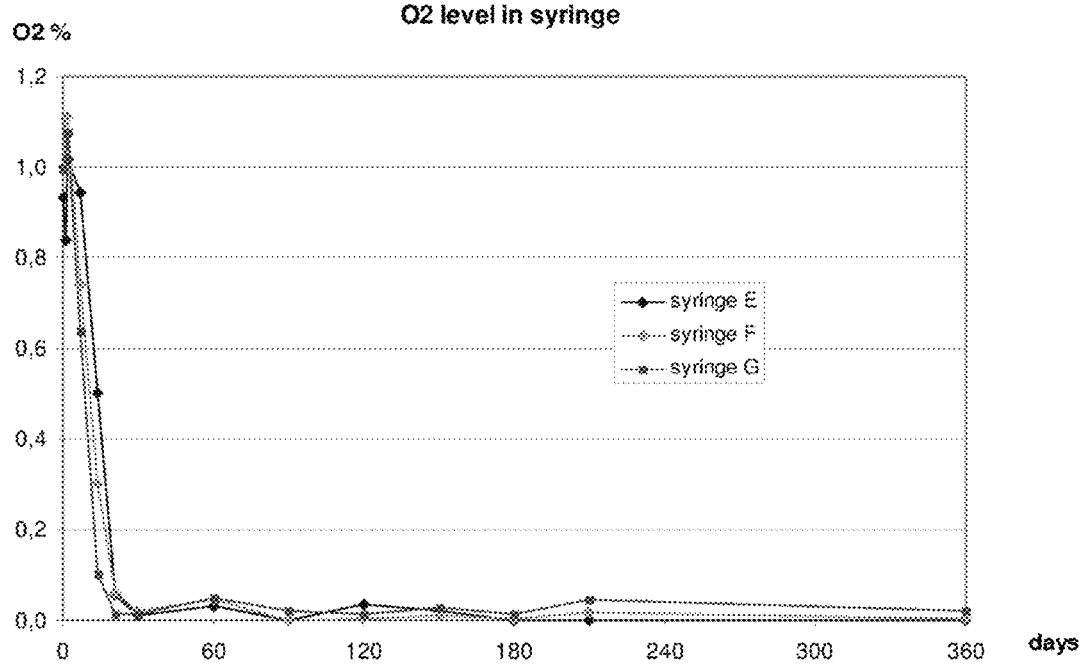

FIG. 9: Oxygen levels in syringe barrels for packaging configurations E, F and G stored at 25° C./60% RH.

Figure 10:
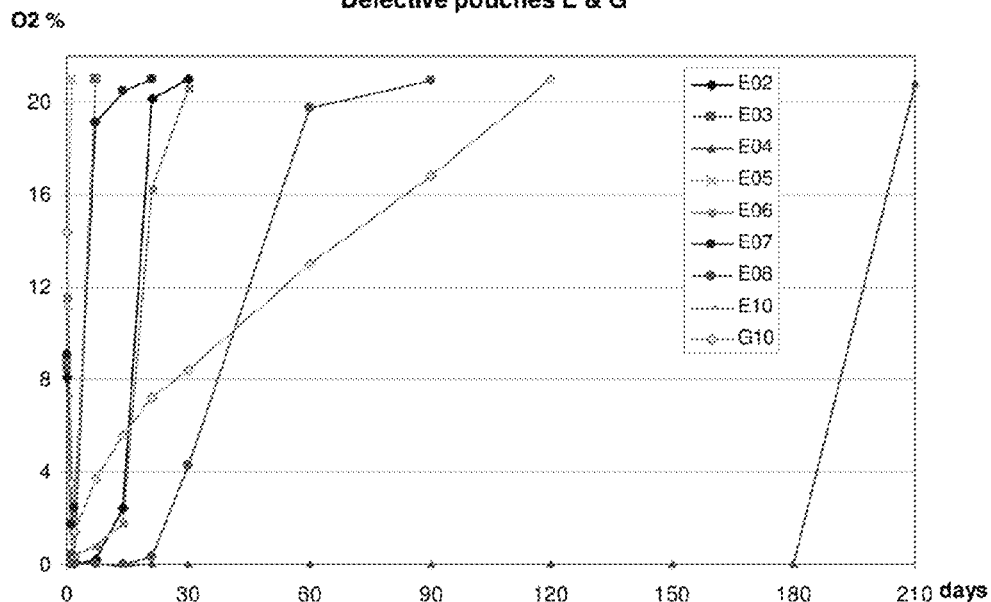

FIG. 10: Oxygen levels in pouch environments of defective pouches of configurations E and G stored at 25° C./60% RH.

Figure 11:
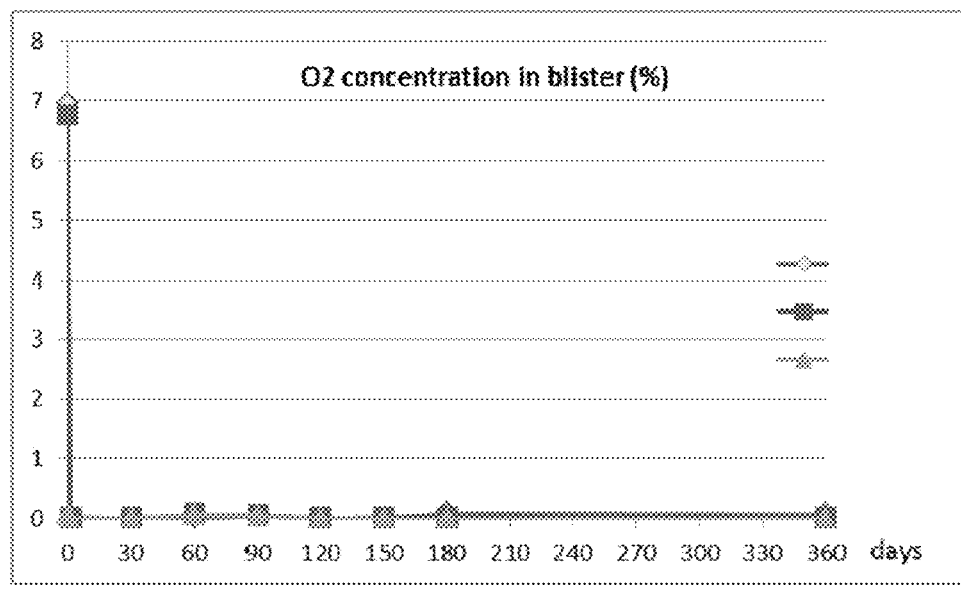

FIG. 11: Oxygen levels in blister environments for packaging configurations 1 (♦), 2 (■), and 3 (▲) stored at 25° C./60% RH.

Figure 12:
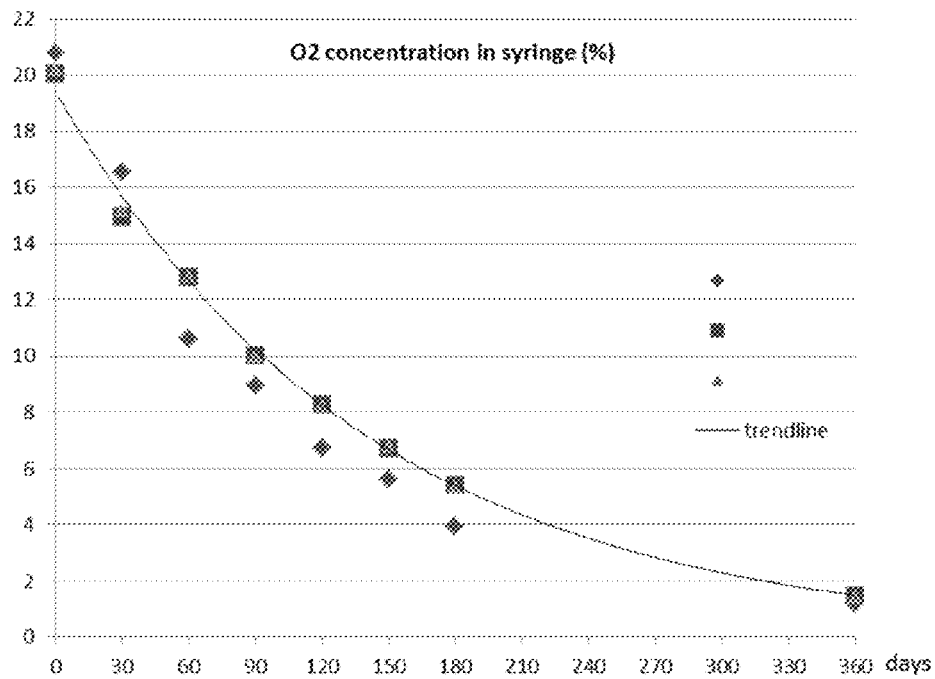

FIG. 12: Oxygen levels in syringe environments for packaging configurations 1 (♦), 2 (■), and 3 (▲) stored at 25° C./60% RH.

Figure 13:
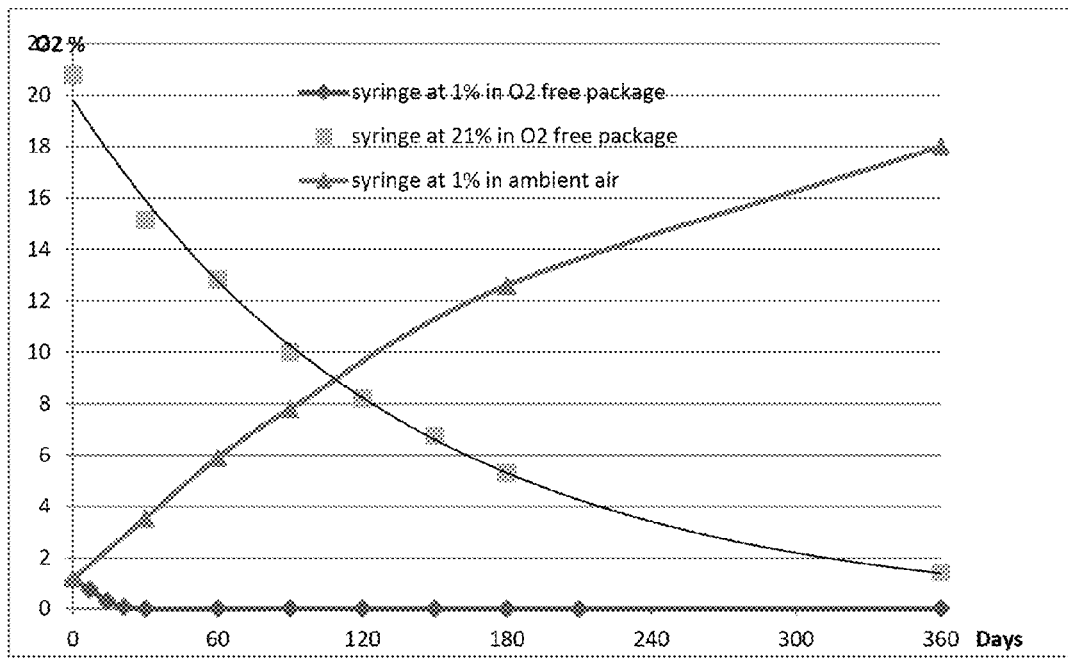

FIG. 13: Oxygen levels in a syringe of various fill and packaging conditions over the course of a year.

Figure 14:
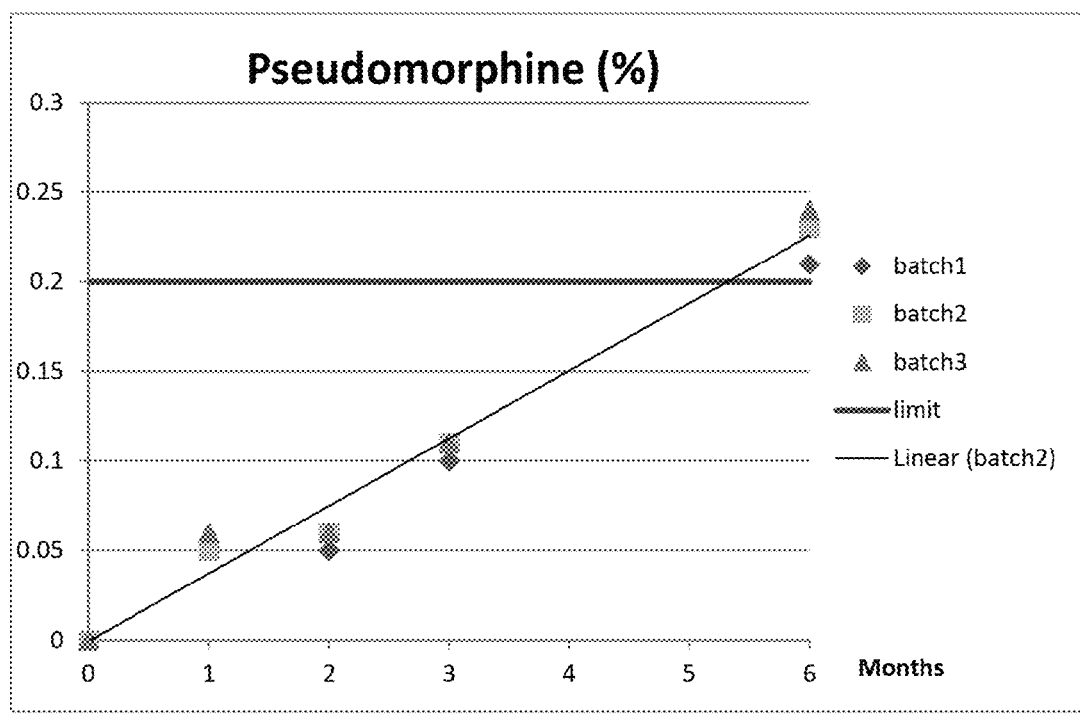

FIG. 14: Pseudomorphine content of 2 mg/mL morphine formulation from Example 5 stored at 40° C./75% RH.

Figure 15:
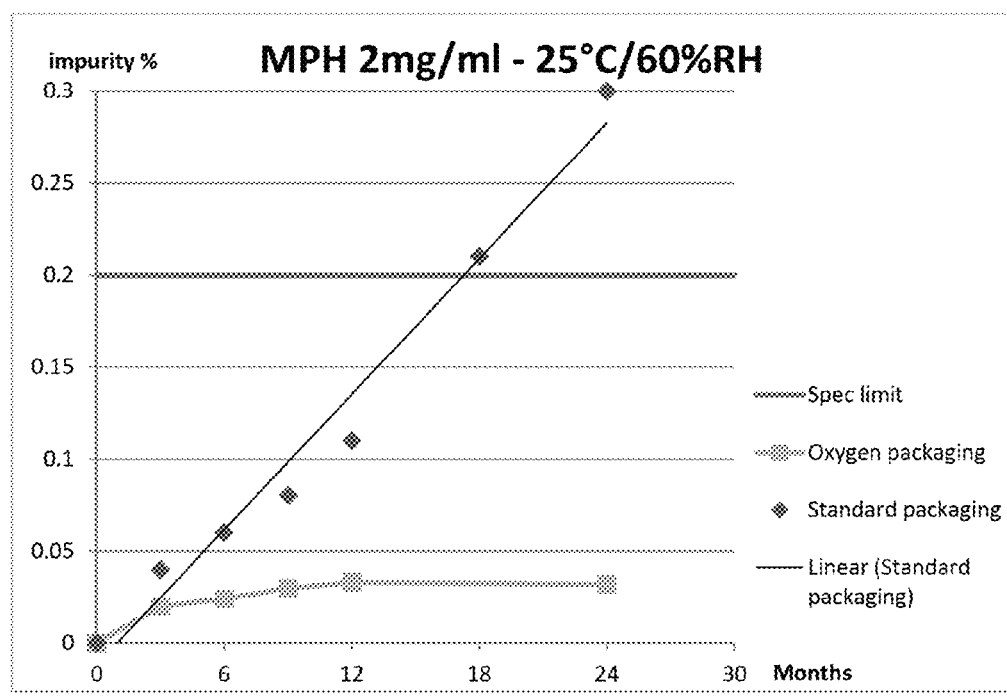
Figure 15:
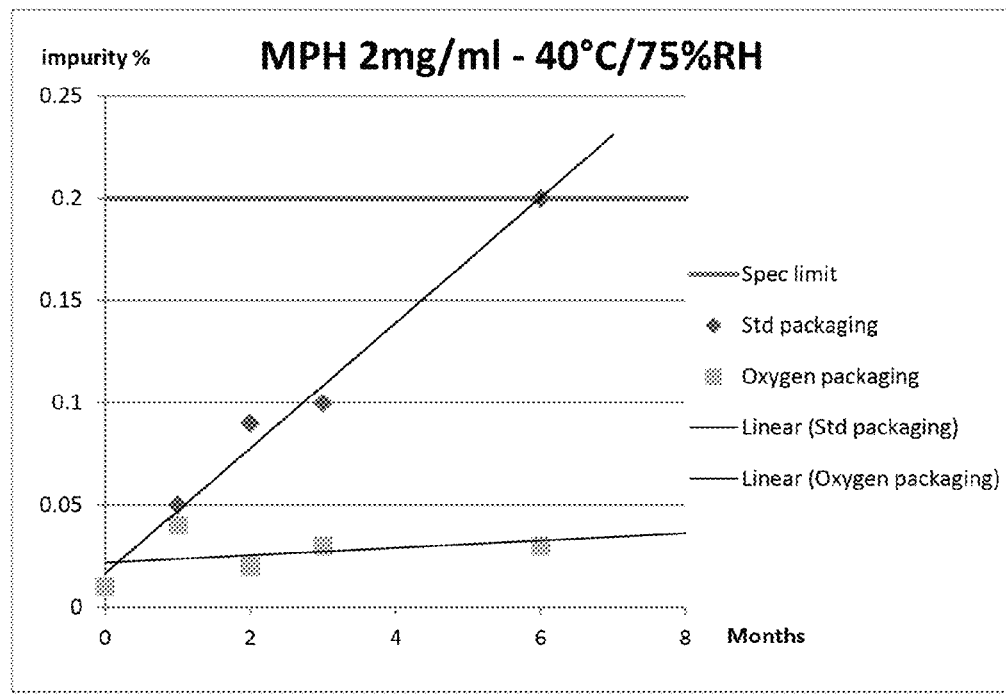

FIG. 15: Pseudomorphine content of 2 mg/mL morphine formulations in (♦) standard packaging and (■) oxygen barrier packaging stored in (top) ambient (25° C./60% RH) or (bottom) accelerated (40° C./75% RH) storage conditions.

Figure 16:
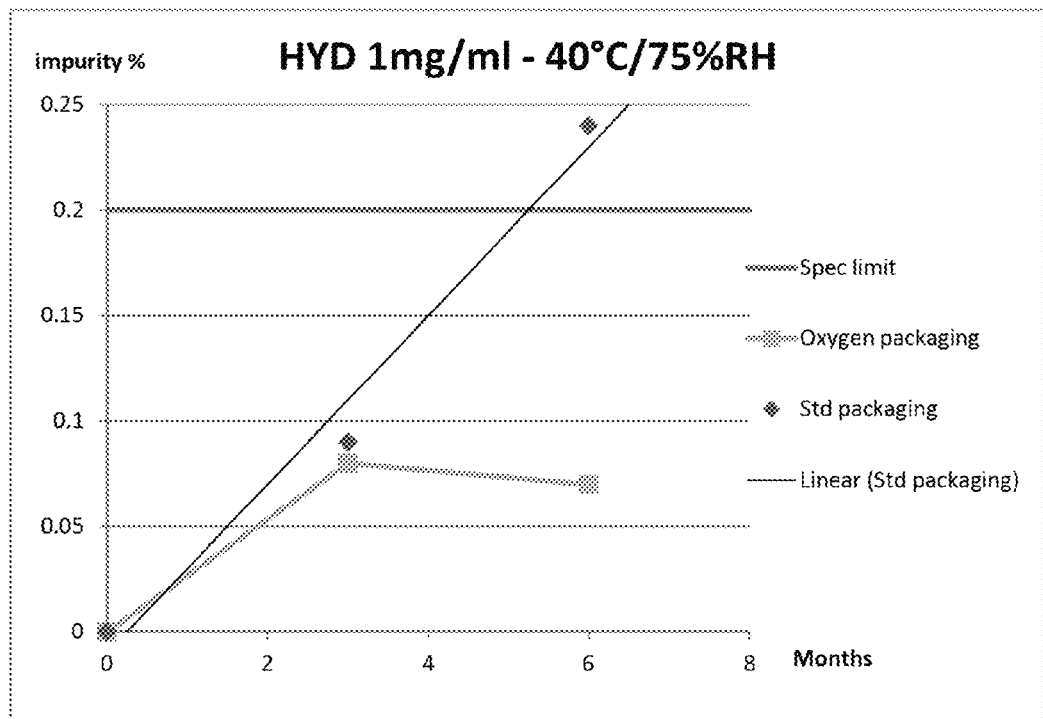
Figure 16:
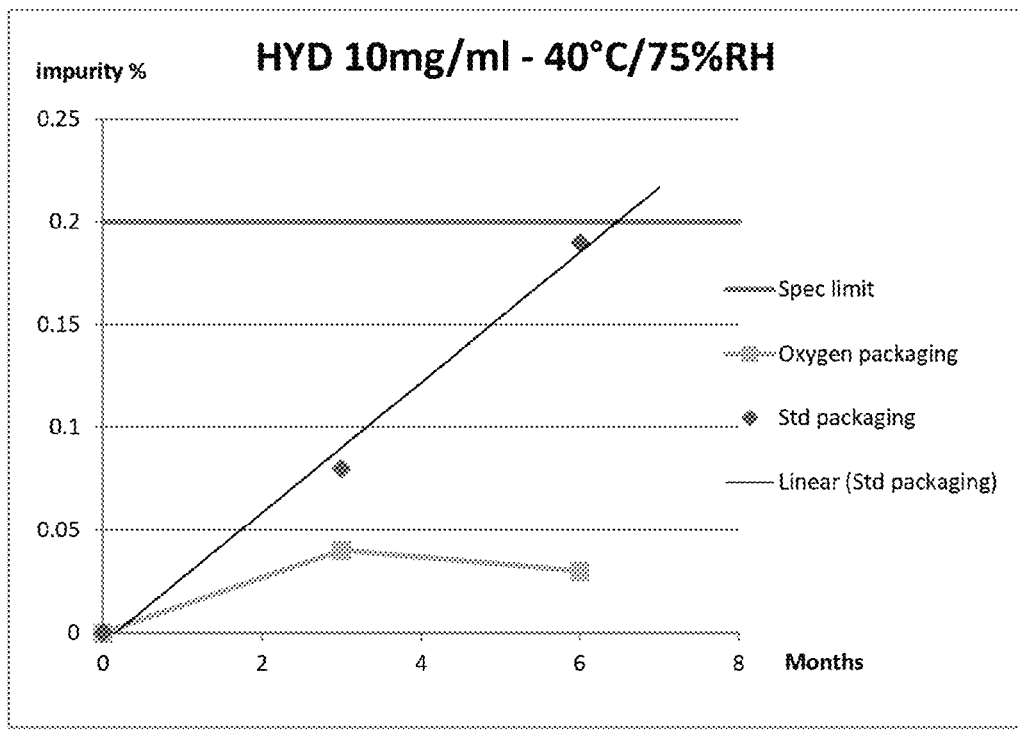

FIG. 16: Unknown impurity content of 1 mg/mL (top) or 10 mg/mL (bottom) hydromorphone formulations in (♦) standard packaging and (■) oxygen barrier packaging stored in accelerated (40° C./75% RH) storage conditions.

Figure 17:
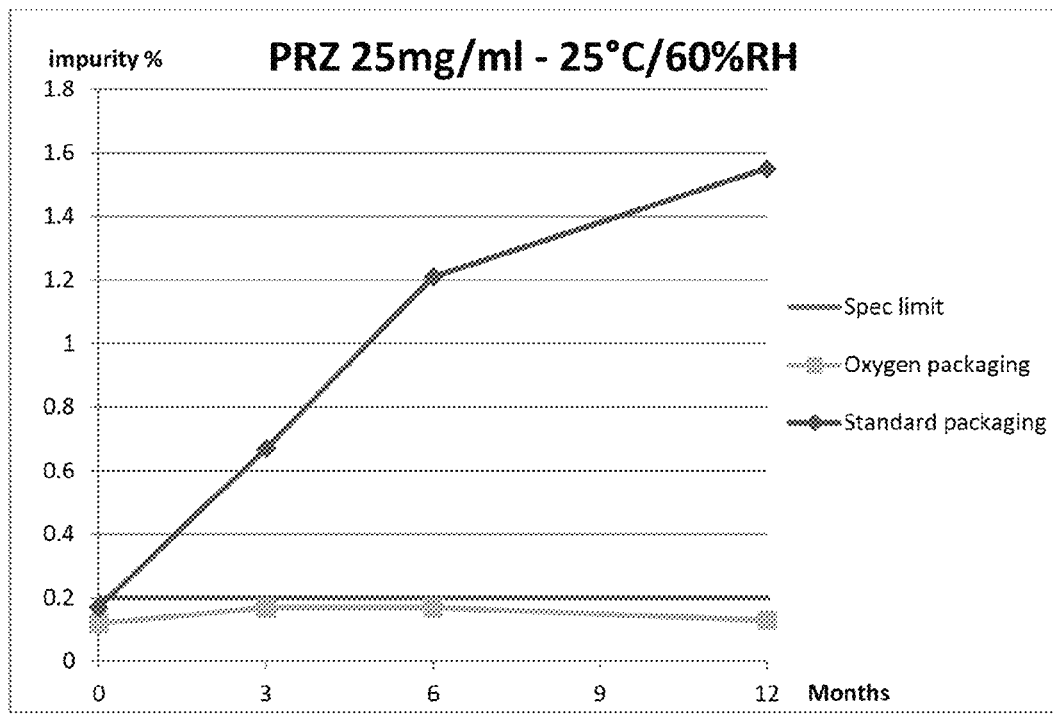
Figure 17:
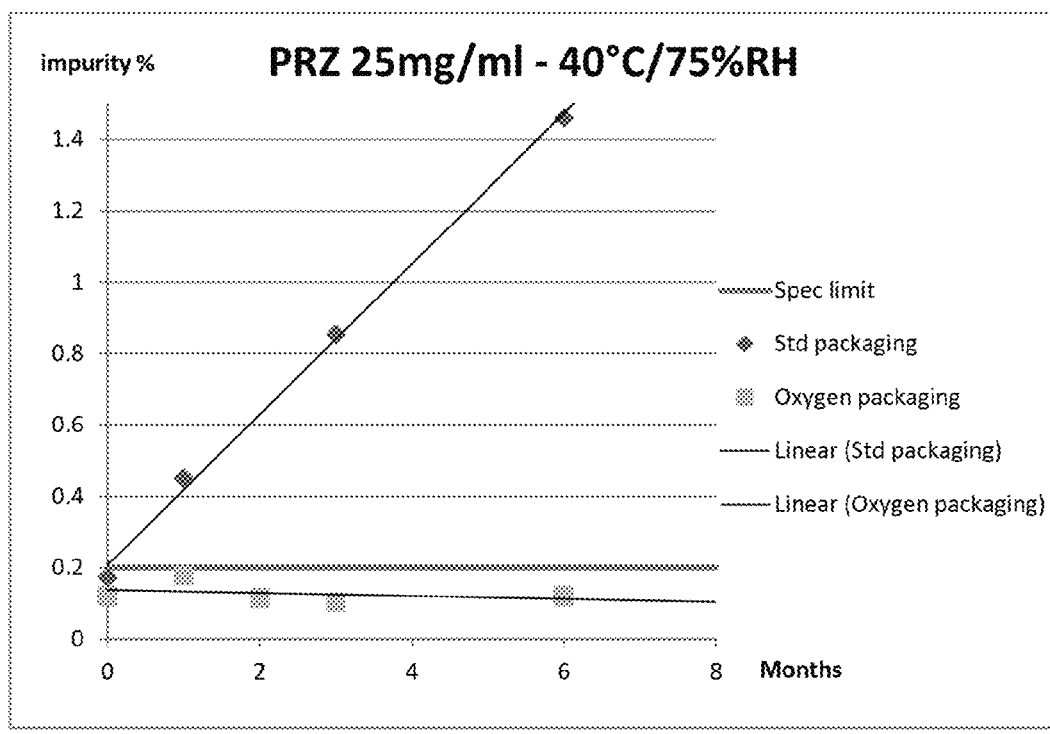

FIG. 17: Sulfoxide content of 25 mg/mL promethazine formulations in (♦) standard packaging and (■) oxygen barrier packaging stored in (top) ambient (25° C./60% RH) or (bottom) accelerated (40° C./75% RH) storage conditions.

DETAILED DESCRIPTION OF THE INVENTION

Provided herein are pharmaceutical packaging systems for prefilled liquid medicament containers having an oxygen permeable component. The packaging systems described herein are useful for enhancing stability and preventing oxidative degradation of oxygen sensitive drugs in liquid form thereby allowing for extended product shelf life and prolonged drug potency or efficiency.

"Oxygen-sensitive" or "oxygen-sensitivity" refers to the ability of a substance to react with oxygen under ambient temperature conditions (e.g., 5° C. to about 40° C.). The chemical reaction may involve the addition of an oxygen atom to the substance, removal of a hydrogen from the substance, or the loss or removal of one or more electrons from a molecular entity, with or without concomitant loss or removal of a proton or protons.

In one aspect, the pharmaceutical packaging systems herein comprise a medicament container as a primary packaging having permeability to oxygen and houses a liquid oxygen sensitive drug; a secondary packaging which envelops the primary packaging and has very low permeability to oxygen and an oxygen absorber that is placed inside or incorporated into the secondary packaging. FIG. 1 illustrates different configurations of the pharmaceutical packaging system embodiments with an oxygen absorber (2) as a sachet (FIG. 1*a*) placed inside the secondary packaging (1) and under the syringe primary packaging (3), in the lid 4 (FIG. 1*b*) of secondary packaging (1) and as a canister (FIG. 1*c*) placed next to the syringe primary packaging. Another embodiment where the oxygen absorber is positioned directly on the syringe primary packaging is also illustrated (FIG. 1*d*). In this case the oxygen absorber can be glued, or bonded directly on the surface of the primary packaging or even integrated in the thickness of the primary packaging. Additional configurations are within the scope of the pharmaceutical packaging systems herein.

A feature of the pharmaceutical packaging systems herein is that the configuration allows the absorption and removal of oxygen in all the components of the system. As the examples show, the oxygen absorber expectedly removes the oxygen from the secondary packaging. However, surprisingly, the oxygen absorber also removes oxygen from the primary packaging container and the liquid as it will be depicted in Example 3. FIG. 2 depicts the oxygen removal of an exemplary pharmaceutical packaging system. Here, the oxygen absorber (2) is placed inside the pharmaceutical packaging system. Therefore, it removes oxygen within the initial air volume present in the secondary packaging (1) at a high transfer rate R3. The absorber also removes the oxygen within the primary packaging container (3) and its contents (in this case a syringe) at a moderately lower transfer rate R2. This oxygen removal is facilitated by the oxygen permeable component of the primary packaging container. Finally, the oxygen absorber of the packaging system removes oxygen from ingress through the secondary packaging over the packaging's shelf life. As the secondary packaging is composed of material that has very low permeability to oxygen, the oxygen transfer rate R1 from the environment outside the secondary packaging is very low.

In essence, the oxygen absorber in the pharmaceutical packaging system herein leads to the absorbance and removal of oxygen in the secondary packaging, the primary packaging and the drug inside the primary packaging. The oxygen absorber further removes the low oxygen ingress through the secondary packaging over time. In this configuration, the residual oxygen amount that is present inside the primary and secondary packaging due to the pharmaceutical manufacturing process as well as the oxygen entering the packaging system from external environments over time, is reduced and even eliminated.

Another feature of the pharmaceutical packaging systems described herein is the pharmaceutical packaging system maintains zero % oxygen level after removal of the initial oxygen in the primary packaging container and secondary packaging for an extended period of time. As a result, the pharmaceutical packaging systems described herein offer increases in the shelf life of oxygen sensitive drugs past conventional packaging and methods such as from inert atmosphere packaging processes (e.g., nitrogen blanketing and/or degassing). In some embodiments, the pharmaceutical packaging systems described herein maintains zero % oxygen level in the primary and secondary packaging for at least about 12 months, at least about 15 months, at least about 18 months, at least about 24 months, at least about 30 months, at least about 36 months, at least about 48 months or at least about 60 months. In certain instances, the pharmaceutical packaging systems described herein maintains zero % oxygen level in the primary and secondary packaging for at least 12 months. In certain instances, the pharmaceutical packaging systems described herein maintains zero % oxygen level in the primary and secondary packaging for at least 24 months. In certain instances, the pharmaceutical packaging systems described herein maintains zero % oxygen level in the primary and secondary packaging for at least 36 months.

Primary Packaging

The primary packaging container of the pharmaceutical packaging systems described herein houses or contains the oxygen sensitive drug in liquid form. Various types of containers are suitable for the containment of oxygen sensitive drugs. Examples of such containers include, without limitation, vials, syringes, ampoules, bottles, cartridges, carpules and i.v. bags or pouches. In some embodiments, the primary packaging container of pharmaceutical packaging systems described herein are selected from a vial, syringe, ampoule, bottle, cartridge, carpule and a bag.

Vials for the containment of the oxygen sensitive drugs generally have open mouths which are normally closed with an elastomer closure through which a hollow needle may be passed and via which liquid may be introduced or removed from the vial. Vials are typically made of type I glass or may be made of plastic such as PET. Suitable elastomers for such closures include, for example, vulcanized elastomers and styrenic block copolymer thermoplastic elastomers, but also natural rubber, acrylate-butadiene rubber, cis-polybutadiene, chlroro or bromobutyl rubber, chlorinated polyethylene elastomers, polyalkylene oxide polymers, ethylene vinyl acetate, fluorosilicone rubbers, hexafluoropropylene-vinylidene fluoride-tetrafluoroethylene terpolymers, butyl rubbers, polyisobutene, synthetic polyisoprene rubber, silicone rubbers, styrene-butadiene rubbers, tetrafluoroethylene propylene copolymers, thermoplastic-copolyesters, thermo-plastic elastomers, or the like or a combination thereof.

Syringes generally comprise a cylindrical barrel, often made of glass but more recently have been made of plastic materials, for example, cyclic olefin polymers or acrylonitrile butadiene styrene (ABS), polycarbonate (PC), polyoxymethylene (POM), polystyrene (PS), polybutylene terephthalate (PBT), polypropylene (PP), polyethylene (PE), polyamide (PA), thermoplastic elastomer (TPE) and their combinations. The barrels of such syringes are operated with an elastomer plunger which can be urged along the barrel to eject liquid content via a nozzle. Suitable elastomers for such plungers may be based on the same thermoplastic elastomers as mentioned above for vial closures. Ampoules are a type of sealed vial which are generally opened by snapping off the neck or the top of the ampoule. Cartridges and carpules are specialized containers that are inserted into a drug delivery device (e.g. syringe or autoinjector). Finally, intravenous bags and pouches are typically used for infusion therapy or multiple dose administration.

For the more rigid primary packaging containers, glass is a suitable material as it provides various benefits. Glass is generally considered to not be permeable to moisture and oxygen permeation. An alternative group of materials, cyclic olefin polymers, polypropylene or polyethylene terephthalate are suitable for the containers as they typically have less breakage concerns as compared to glass and still exhibit good transparency. These materials include cyclic olefin copolymers such as Topas™ polymer(Topas Advanced Polymers GmbH) and cyclic olefin homopolymers such as Crystal Zenith™ polymer (Daikyo). For flexible primary packaging containers such as bags, materials suitable include those having oxygen barrier properties.

Regarding drugs with sensitivity to light, the primary packaging container should have light barrier properties that can be achieved with a colorant to produce a colored (e.g., amber, dark blue) or opaque primary packaging container. A primary packaging made of transparent materials may also be suitable provided it is placed in secondary or tertiary packaging materials that are opaque to light.

In one embodiment of the pharmaceutical packaging systems described herein, the primary packaging container is a syringe. Syringes, and in particular hypodermic syringes, are useful in the medical field for dispensing fluids, including medications. A conventional syringe typically includes a syringe barrel with in an opening at one and a plunger mechanism disposed through the opposite end. Syringes in the pharmaceutical packaging systems described herein contain the liquid drug for dispensing and are stored overtime once filled. They are referred to as "pre-filled" syringes. An advantage of the pre-filled syringe is that the drug is filled at a proper dose and can be delivered to a patient quickly over conventional methods of filling the syringe with the liquid drug in a vial prior to administration, thereby saving time, maintaining consistent dosing and volumes for delivery and ending contamination and degradation issues of multiple dose drug vials. Exemplary syringes for use in the pharmaceutical packaging systems described herein include those described in U.S. Pat. Nos. 6,196,998; 6,200,627; 6,217,550; 6,743,216; 7,141,042; 8,075,535; and 8,652,094; and U.S. Pat. Appl. No. 2013/0081974 each of which is incorporated by reference for their disclosure relating to syringe assembly.

In the pharmaceutical packaging systems described herein, the primary packaging container also has an oxygen permeable component. "Oxygen-permeable" as used herein refers to materials which allow the passage of oxygen through the material. Certain rubbers, plastics and papers have oxygen-permeable properties and can be molded into stoppers, caps, seals, membranes and other components which may be structural or protective. When an oxygen-permeable component separates two different oxygen level environments, the oxygen-permeable component allows the passage of oxygen from the higher oxygen level environment to the lower oxygen level environment. Over time, the two environments equilibrate with respect to oxygen levels. Usually, these materials are also permeable to other gases. As such, the oxygen-permeable component allows for sterilization processes such as via gas (e.g., ethylene oxide) or steam sterilization. For example, a syringe primary packaging container can have a tip cap that is gas or oxygen-permeable which allows sterilization of the syringe interior, and if the syringe is filled, also the drug itself. Accordingly, in some embodiments, the primary packaging container is a syringe that has an oxygen-permeable tip cap which can be a single material tip cap or a bi-material tip cap. In an exemplary embodiment, the syringe oxygen-permeable tip cap includes a rubber part. Exemplary tip caps include those described in U.S. Pat. Nos. 5,624,402; 6,027,482 and 6,190,364, each of which is incorporated by reference for their disclosure relating to tip caps.

Secondary Packaging

The secondary packaging component of the pharmaceutical packaging systems described herein envelops or surrounds the primary packaging container that holds the liquid drug. In the embodiments herein, after placement of the primary packing container into the secondary packaging, the secondary packaging is sealed to prevent any contamination as well as ingress of oxygen. To prevent further ingress of oxygen into the secondary packaging, the secondary packaging is composed with an oxygen barrier material which has very low permeability to oxygen molecules. The secondary packaging can be of any packaging type suitable for the primary packaging container, the types which includes, without limitation, a bag, a pouch, a box, a bag, a blister, a canister, a bottle and the like. As such, the secondary packaging may be rigid or flexible and of any shape and size. The exact requirements of a secondary packaging depends on a variety of factors, including the chemical nature of the drug inside the primary packaging container, amount and type of the oxygen absorber, physical configuration of the primary packaging container, hermetic sealing method, nitrogen blanketing, vacuumization and/or other modified atmosphere inside the secondary packaging, initial oxygen concentration inside the secondary packaging, intended shelf life of the drug, etc.

Oxygen barrier materials for the secondary packaging have very low permeability to oxygen molecules (e.g., ~1 or less $cm^3O_2/m^2$ per day, atm). Non-limiting examples of oxygen barrier materials suitable for the secondary packing include ethylene vinyl alcohol (EVOH), polyvinyl alcohol (PVOH), polyvinyl chloride (PVC), polyvinylidene chloride (PVDC), polychlorotrifluoroethylene (PCTFE), vinylidene chloride/methyl acrylate copolymer, polyamide, and polyester. Metal foil (e.g., aluminum) or SiOx compounds can be used to provide very low permeability to oxygen in the secondary packaging. Metalized films can include a sputter coating or other application of a metal layer such as aluminum to a polymeric substrate such as high density polyethylene (HDPE), low density polyethylene (LDPE), ethylene/vinyl alcohol copolymer (EVOH), polypropylene (PP), polyethylene terephthalate (PET) including amorphous forms (APET) and glycol modified forms (PET-G), polyethylene naphthalate (PEN), ethylene acrylic acid copolymer (EAA), and polyamide (PA). Alternatively, oxide coated webs (e.g., aluminum oxide or silicon oxide) can be used to provide very low permeability to oxygen in the secondary packaging. Oxide coated films can include a coating or other application of the oxide, such as alumina or silica, to a polymeric substrate such as high density polyethylene (HDPE), low density polyethlyene (LDPE), ethylene/vinyl alcohol copolymer (EVOH), polypropylene (PP), polyethylene terephthalate (PET) including amorphous forms (APET) and glycol modified forms (PET-G), polyethylene naphthalate (PEN), ethylene acrylic acid copolymer (EAA), and polyamide (PA). In some embodiments, the secondary packaging comprises an oxygen barrier material selected from the group consisting of EVOH, PVOH, PVC, PVDC, PCTFE, vinylidene chloride/methyl acrylate copolymer, polyamide, polyester, a metalized film, oxide coated films, and combinations thereof.

Embodiments of the oxygen barrier materials can be present in the form of multilayer films. Multilayer films (e.g., 2, 3, 4, 5 or 6 layer films) can comprise one or more of the previously described oxygen barrier material(s), and may include additional layers of non-barrier materials such as PET, polyethylene (PE) and/or coated (e.g., clay, wax, plastic, or the like) or uncoated paper. Suitable multilayer films include, but are not limited to, PVC/EVOH, PET/EVOH, PET/EVOH/PE, PET/EVOH/PET, PE/EVOH/PE, PVC/PCTFE/EVOH, Paper/Aluminum (Alu)/PE, PET/Alu/PE, Paper/PE/foil/PE, Paper/PET/Alu, Clay-coated paper/PE/foil/LDPE, Paper/LDPE/foil/EEA, and related films thereof. Layers can be bonded together via the use of adhesives, for example, a polyolefin blend (mixture of poly(a-olefins), or polyamide resins. In some embodiments, the secondary packaging comprises an oxygen barrier material as a multilayer film. In certain instances the multilayer film is PVC/EVOH, PET/EVOH, PET/EVOH/PE, PET/EVOH/PET, PE/EVOH/PE, PVC/PCTFE/EVOH, Paper/Aluminum (Alu)/PE, PET/Alu/PE, Paper/PE/foil/PE, Paper/PET/Alu, Clay-coated paper/PE/foil/LDPE or Paper/LDPE/foil/EEA.

Multilayer films are made by any known method, including conventional extrusion, coextrusion, and/or lamination processes. Likewise, conventional manufacturing processes can be used to make a bag, a pouch, a box, a bag, a blister, a canister, a bottle or other container from the oxygen barrier materials for the secondary packaging as well as to provide hermetic sealing. Hermetic sealing has importance in the pharmaceutical packaging systems described herein to maintain the reduced oxygen level. Indeed, when the secondary packaging is improperly sealed or leaking, the oxygen level can increase rapidly to 21% after oxygen scavenger is fully at capacity as demonstrated in Example 4. Optionally, in some embodiments, the hermetic sealing occurs under an inert environment (e.g., nitrogen blanket) to reduce the initial oxygen levels in the secondary packaging's air volume.

In some embodiments, the secondary packaging is a blister packaging. Blister packaging is known in the packaging industry and commonly used for packaging pharmaceuticals and medical devices such as solid dosage forms (tablets, capsules, etc.), transdermal patches, syringes, and the like. The term "blister" refers to a bottom web substrate that is rigid and has one or more recesses that conform and can hold in place the contents being packaged (in this case the primary packaging container). The recesses can be formed by thermoforming, a deforming process such as an aluminum-based cold forming process or by injection molding. For the pharmaceutical packaging systems described herein where the secondary packaging is a blister packaging, bottom web substrate comprises an oxygen barrier material (e.g., multilayer film with an EVOH layer). Depending on materials used and on the nature of the drugs stored inside the primary packaging, bottom web substrate can be transparent or opaque with the use of colorants.

Another component of a blister packaging is a top web laminate ("lid") which is laminated to the blister by heat seal. The top web lid is usually flexible and can be peeled off the blister to allow access to the packaged contents. For embodiments where the secondary packaging is a blister packaging, the top web lid also comprises an oxygen barrier material, such as metal (e.g., aluminum) foil. In certain instances, the top web lid comprises a multilayer film having an aluminum layer and one or more additional layers. Additional layers include coated or uncoated paper, PE and/or PET layers. In certain instances, the top web lid comprises a film comprising paper, aluminum and PET layers. The top web lid also comprises a laminate for sealing the blister. The laminate is applied to the lid by methods known in the packaging industry including coating, extrusion and lamination. One type of laminate is a heat-sealable laminate (e.g., thermo-plastic coating). The top lid laminate also encompasses other adhesive technologies, including pressure sensitive adhesives, photo-curing adhesives and two component (e.g., epoxy) adhesives.

In an exemplary embodiment, the secondary packaging comprises of a blister packaging having a thermoformed transparent shell made of a multilayer plastic film that includes EVOH (bottom web), and a multilayer paper-plastic heat salad lid material including an aluminum layer (top web).

In a further embodiment, a secondary packaging container suitable for the pharmaceutical packaging systems described herein is provided which includes a first compartment to receive a syringe barrel and second compartment to receive a plunger rod separate and detached from the syringe barrel. With the syringe barrel received in the first compartment and the plunger rod received within the second compartment, the sealing member of the plunger rod seals the syringe barrel and the plunger rod within the secondary packaging. This secondary packaging container configuration allows for reduced storage space of the syringe. In this manner, upon removal of the plunger rod and the syringe barrel from the secondary packaging, the plunger rod can quickly and easily be secured to the syringe barrel via a stopper for delivery of a drug formulation contained inside the syringe. An exemplary syringe and secondary packaging configuration is depicted in FIG. 3. FIG. 3 shows a syringe barrel (30) containing a drug formulation with a sealing cap (20) and a flange (40) for a user's fingers received in a first compartment portion (108) and a plunger rod (14) received in a second compartment portion (94) of a secondary packaging (92). The plunger rod (14) can comprise elastic fingers (160) which lock and secure to the syringe barrel (30), a flange (66) for usability, key slots (78) for securing the plunger rod in the second compartment of the secondary packaging and vents (76) to allow oxygen removal with an oxygen absorber (not shown). The secondary packaging with the syringe components is sealed with a sealing cover (190). Additional secondary packaging configurations for pharmaceutical packaging systems described herein are found in U.S. Pat. Appl. No. 2013/0080974, which is incorporated by reference for the relating to syringe and packaging assembly.

Oxygen Absorber

In the pharmaceutical packaging systems described herein, oxygen absorbers absorb and remove oxygen from all components of the system. Oxygen absorbers are contemplated to be in any size or shape including sachet, pouch, capsule, label, strip, patch, canister, cartridge, lining, sticker, etc. that is placed inside of the secondary packaging as well as part of the secondary packaging itself but can also be integrated to the primary packaging. In some embodiments, the oxygen absorber is in the form of a sachet. In other embodiments, the oxygen absorber is in the form of a canister. In some other embodiments, the oxygen absorber is in the form of a label. In yet other embodiments, the oxygen absorber is in the form of a strip. In further embodiments, the oxygen absorber is a sticker or label that adheres to the secondary packaging or to the primary packaging. In yet further embodiments, the oxygen absorber is incorporated as part of the secondary packaging itself such as lid, film, or seal of the secondary packaging. Non-limiting examples of secondary packaging and oxygen absorber configurations are depicted in FIG. 1. An exemplary secondary packaging with an oxygen absorber for a morphine formulation is described in Example 8.

Suitable materials for oxygen absorbers include metal-based substances that remove oxygen by reacting with it by chemical bonding, generally forming a metal oxide component. Metal-based substances include elemental iron as well as iron oxide, iron hydroxide, iron carbide and the like. Other metals for use as oxygen absorbers include nickel, tin, copper and zinc. Metal-based oxygen absorbers are typically in the form of a powder to increase surface area. Powder formation of the metal-based oxygen absorbers is by any known method including, but not limited to, atomization, milling, pulverization, and electrolysis. Additional materials for oxygen absorbers include low molecular weight organic compounds such as ascorbic acid, sodium ascorbate, catechol and phenol, activated carbon and polymeric materials incorporating a resin and a catalyst. In some embodiments of the pharmaceutical packaging system, the oxygen absorber is a metal-based oxygen absorber. In certain instances of the pharmaceutical packaging system, the oxygen absorber is an iron-based oxygen absorber. In further instances of the pharmaceutical packaging system, the oxygen absorber is an iron-based oxygen absorber in the form of a canister.

Oxygen Absorbers and Secondary Packaging

A feature of the oxygen absorber in the pharmaceutical packaging systems herein is the rapid uptake of oxygen present in the secondary packaging. Oxygen in air at ambient temperature and pressure (1 atm) is at a concentration of about 21%. When a pharmaceutical packaging system described herein is assembled in air in ambient conditions, the environment inside the secondary packaging is initially also at 21% oxygen level. In Example 3 and FIGS. 7 and 8, the oxygen absorber in the pharmaceutical packaging system quickly reduces the oxygen level in the secondary packaging to zero % in one to three days. Accordingly, in some embodiments, the oxygen absorber reduces oxygen to zero % in the secondary packaging in about seven days, in about six days, in about five days, in about four days, in about three days, in about two days, or in about one day after initial packaging assembly. In some embodiments, the oxygen absorber reduces oxygen to zero % in the secondary packaging in about one to seven days. In some embodiments, the oxygen absorber reduces oxygen to zero % in the secondary packaging in about one to three days. In some embodiments, the oxygen absorber reduces oxygen in the secondary packaging by about 35%, about 50%, about 60%, about 65%, about 70%, about 75%, about 80%, about 85%, about 90%, or about 95% of the total oxygen in the air per day after initial packaging assembly. In certain instances, the oxygen absorber reduces oxygen in the secondary packaging by about 50% per day. In other instances, the oxygen absorber reduces oxygen in the secondary packaging by about 75% per day. In further instances, the oxygen absorber reduces oxygen in the secondary packaging by about 90% per day. In other embodiments, the oxygen absorber reduces oxygen in the secondary packaging by about 35% to about 75%, about 50% to about 80%, or about 65% to about 90% per day after initial packaging assembly.

In further embodiments, the oxygen absorber reduces about 2 to about 10 cc of oxygen/day, atm; about 3 to about 8 cc of oxygen/day, atm; or about 4 to 6 cc of oxygen/day, atm in the secondary packaging. In certain instances, the oxygen absorber reduces about 2, about 3, about 4, about 5, about 6, about 7, about 8, about 9, or about 10 cc of oxygen/day, atm in the secondary packaging. In some instances, the oxygen absorber reduces about 4 cc of oxygen/day, atm. In other instances, the oxygen absorber reduces about 6 cc of oxygen/day, atm. In further instances, the oxygen absorber reduces about 8 cc of oxygen/day, atm.

Another feature of the oxygen absorber is that it maintains zero % oxygen level after removal of the initial oxygen in the secondary packaging for an extended period of time. In some embodiments, the oxygen absorber maintains zero % oxygen level in the secondary packaging for the entire shelf life of the drug. In some embodiments, the oxygen absorber maintains zero % oxygen level in the secondary packaging for at least about 12 months, at least about 15 months, at least about 18 months, at least about 24 months, at least about 30 months, at least about 36 months, at least about 48 months or at least about 60 months. In certain instances, the oxygen absorber maintains zero % oxygen level in the secondary packaging for at least 12 months. In certain instances, the oxygen absorber maintains zero % oxygen level in the secondary packaging for at least 24 months. In certain instances, the oxygen absorber maintains zero % oxygen level in the secondary packaging for at least 36 months.

Oxygen Absorbers and Primary Packaging

An advantageous feature of the oxygen absorber in the pharmaceutical packaging systems herein is the absorbance and removal of oxygen present in the primary packaging and in the liquid drug itself. Surprisingly, it was found that the oxygen absorber in exemplary packaging systems also removed residual oxygen in the primary packaging and in the liquid over time to zero % oxygen level. Degassed liquids by nitrogen bubbling still contain approximately 1% residual oxygen level, or approximately 400 parts per billion (ppb) oxygen, or approximately a partial pressure of 7.6 mmHg. As it will be illustrated and described later in the description referring to Example 3 and FIG. 9, the oxygen absorber in exemplary pharmaceutical packaging systems reduced the residual oxygen level (approximately %1) in the primary packaging and the liquid inside to zero % in one to three months. Thus, in some embodiments, the oxygen absorber reduces oxygen to zero % in the primary packaging in about three months, in about two months, or in about one month after initial primary packaging assembly under inert conditions. In some embodiments, the oxygen absorber reduces oxygen in the primary packaging by about 35%, about 50%, about 60%, about 65%, about 70%, about 75%, about 80%, about 85%, about 90%, or about 95% of the residual oxygen per month after initial primary packaging assembly under inert conditions. In certain instances, the oxygen absorber reduces oxygen in the primary packaging by about 50% per month. In other instances, the oxygen absorber reduces oxygen in the primary packaging by about 75% per month. In further instances, the oxygen absorber reduces oxygen in the primary packaging by about 90% per month. In other embodiments, the oxygen absorber reduces oxygen in the primary packaging by about 35% to about 75%, about 50% to about 80%, or about 65% to about 90% per month.

In other embodiments, the oxygen absorber reduces oxygen in the primary packaging by about 150 ppb oxygen, about 200 ppb oxygen, about 250 ppb oxygen, about 300 ppb oxygen, about 350 ppb oxygen or about 400 ppb oxygen in the liquid contained in the primary packaging per month after initial primary packaging assembly under inert conditions. In certain instances, the oxygen absorber reduces oxygen in the liquid contained in the primary packaging by about 200 ppb oxygen per month. In other instances, the oxygen absorber reduces oxygen in the liquid contained in the primary packaging by about 300 ppb oxygen per month. In further instances, the oxygen absorber reduces oxygen in the liquid contained in the primary packaging by about 400 ppb oxygen per month. In other embodiments, the oxygen absorber reduces oxygen in the liquid contained in the primary packaging by about 150 ppb to about 300 ppb oxygen, about 250 ppb to about 350 ppb oxygen, or about 300 ppb to about 400 ppb oxygen per month after initial primary packaging assembly under inert conditions.

In further embodiments, the oxygen absorber reduces the oxygen partial pressure in the primary packaging by about 2.5 mmHg, about 3.0 mmHg, about 3.5 mmHg, about 4.0 mmHg, about 4.5 mmHg, about 5.0 mmHg, about 5.5 mmHg, about 6.0 mmHg, about 6.5 mmHg, about 7.0 mmHg or about 7.5 mmHg in the liquid contained in the primary packaging per month after initial primary packaging assembly under inert conditions. In certain instances, the oxygen absorber reduces oxygen partial pressure in the liquid contained in the primary packaging by about 2.5 mmHg per month. In other instances, the oxygen absorber reduces oxygen partial pressure in the liquid contained in the primary packaging by about 5.0 mmHg per month. In further instances, the oxygen absorber reduces oxygen partial pressure in the liquid contained in the primary packaging by about 7.5 mmHg per month. In other embodiments, the oxygen absorber reduces oxygen partial pressure in the liquid contained in the primary packaging by about 2.5 mmHg to about 5.0 mmHg, about 3.5 mmHg to about 6.0 mmHg, or about 5.0 mmHg to about 7.5 mmHg per month after initial primary packaging assembly under inert conditions.

The oxygen absorber, in some embodiments, also maintains zero % oxygen level after removal of the initial oxygen in the primary packaging for an extended period of time. In some embodiments, the oxygen absorber maintains zero % oxygen level in the primary packaging for the entire shelf life of the drug. In some embodiments, the oxygen absorber maintains zero % oxygen level in the primary packaging for at least about 12 months, at least about 15 months, at least about 18 months, at least about 24 months, at least about 30 months, at least about 36 months, at least about 48 months or at least about 60 months. In certain instances, the oxygen absorber maintains zero % oxygen level in the primary packaging for at least 12 months. n certain instances, the oxygen absorber maintains zero % oxygen level in the primary packaging for at least 24 months. In certain instances, the oxygen absorber maintains zero % oxygen level in the primary packaging for at least 36 months.

An interesting property of the pharmaceutical packaging systems herein, is that after removal of oxygen in the primary and secondary packaging by the oxygen absorber, the air pressure in the secondary packaging environment achieves lower than atmospheric pressure, such that there is vacuum effect.

Oxygen Absorber Capacities

The capacity for absorbing oxygen for the oxygen absorbers of the pharmaceutical packaging systems described herein encompass the capacities sufficient to reduce the initial oxygen levels of the primary and secondary packaging to a zero % oxygen level at a rate as described in the previous embodiments and maintain the zero % oxygen level for a period of time as described in the previous embodiments. The oxygen absorbing capacity can be optimized according to the materials used in secondary packaging, the surface area of the secondary packaging and amount of initial oxygen in the secondary and primary packaging. For example, the oxygen absorbing capacity of the absorber is decreased when secondary packaging has very low permeability to oxygen whereas the oxygen absorbing capacity of the absorber is increased when secondary packaging is made from material that is more permeable to oxygen. This is illustrated in more detail in Example 3 and FIG. 7. It is also within the scope of embodiments of the pharmaceutical packaging systems described herein, that the oxygen absorbing capacity is greater than needed for the total amount of oxygen over the shelf life of the pharmaceutical packaging system, i.e., overfill capacity. The extra capacity can allow for a larger buffer in the handling process for assembly of the pharmaceutical packaging system.

Exemplary oxygen absorber capacities, in some embodiments, range from about 10 cc ($cm^3$, atm) to about 50 cc oxygen absorbance capacity, from about 15 cc to about 40 cc oxygen absorbance capacity, or from about 20 to about 30 cc oxygen absorbance capacity. In some embodiments, the oxygen absorber capacity of the oxygen absorber in the pharmaceutical packaging system is about 10 cc, about 15 cc, about 20 cc, about 25 cc, about 30 cc, about 35 cc, about 40 cc, about 45 cc, or about 50 cc oxygen absorbance capacity. In certain instances, the oxygen absorber capacity of the oxygen absorber in the pharmaceutical packaging system is about 15 cc. In certain instances, the oxygen absorber capacity of the oxygen absorber in the pharmaceutical packaging system is about 30 cc.

Packaging Assembly

In preparation of pharmaceutical packaging systems described herein, the packaging is, in some embodiments, assembled in an environment containing an inert gas, i.e., under inert packaging conditions, to lower the initial oxygen concentration in the primary and/or secondary packaging. Under inert packaging conditions include the use of flushing or blanketing a primary and/or secondary packaging container with an inert gas as well as degassing a drug formulation by inert gas. The use of an inert gas (e.g., nitrogen, argon, $CO_2$, helium and the like) limits the drug formulation to oxygen exposure. In some embodiments, the liquid drug formulation is also sparged or bubbled by the inert gas to remove oxygen in the liquid. The solutions are then filled and sealed into primary containers and, in some embodiments, secondary packaging under inert gas.

The pharmaceutical packaging systems described herein can remove oxygen from a primary packaging container that is packaged under ambient conditions (where the oxygen concentration is about 21%) as depicted in Example 5 and FIG. 12. However, oxygen removal from a level 21% is slow, as shown in the example, and therefore, primary packaging in ambient conditions is not recommended as the large amount of residual oxygen may cause degradation prior to its slow removal.

Oxygen Sensitive Drugs

As used herein, the term "drug" refers to a pharmaceutically active ingredient(s) and any pharmaceutical liquid composition containing the pharmaceutically active ingredient(s). Pharmaceutical liquid compositions include forms such as solutions, suspensions, emulsions and the like). These pharmaceutical liquid compositions can be administered orally or by injection.

Any drug that is oxygen sensitive, i.e., can degrade as a result of exposure to oxygen, is suitable for incorporation into the pharmaceutical packaging systems described herein. Oxygen sensitive drugs include those that have amines either as salts or free bases, sulfides, allylic alcohols, phenols and other chemical groups that can have reactivity with oxygen. Non-limiting examples of oxygen sensitive drugs include morphine, hydromorphone, promethazine, dopamine, epinephrine, norepinephrine, esterified estrogen, ephedrine, pseudoephedrine, acetaminophen, ibuprofen, danofloxacin, erythromycin, penicillin, cyclosporine, methyldopate, cetirizine, diltiazem, verapamil, mexiletine, chlorothiazide, carbamazepine, selegiline, oxybutynin, vitamin A, vitamin B, vitamin C, L-cysteine, L-tryptophan and the like. In some embodiments, the primary packaging container of the pharmaceutical packaging systems described herein contain morphine. In other embodiments, the primary packaging container of the pharmaceutical packaging systems described herein contain hydromorphone. In further embodiments, the primary packaging container of the pharmaceutical packaging systems described herein contain promethazine.

The oxygen sensitive drugs in the pharmaceutical packaging systems described herein are stable in various storage conditions including ambient, intermediate and accelerated conditions. Stability as used herein refers to a formulation meeting all stability criteria along its particular shelf life, as defined in the USP or equivalent monograph of the drug product (for the assay of the drug substance in particular) and the current stability criteria of the ICH Q3B guidance for impurities. All critical quality attributes need to stay in their acceptance range throughout the formulation's shelf life. As an example, for a morphine formulation to be stable, assay of the drug substance ,i.e., morphine, is in the [90.0% -110.0%] range as per USP and per ICH Q3B guidelines, all known, i.e., identified, degradation products, such as pseudomorphine, hydroxymorphine, norphine-N-oxide, and the like, as well as unknown degradation products need to be no more than (NMT) 0.2%. Stability of the oxygen sensitive drugs in the pharmaceutical packaging systems described herein is assessed by HPLC, UPLC or any other known analytical method.

In some embodiments an oxygen sensitive drug, when stored in the pharmaceutical packaging systems described herein, is stable in ambient conditions (e.g., 25° C./60% RH) for at least 12 months, at least 15 months, at least 18 months, or at least 24 months. In certain instances, an oxygen sensitive drug, when stored in the pharmaceutical packaging systems described herein, is stable in ambient conditions for at least 24 months. In other embodiments an oxygen sensitive drug, when stored in the pharmaceutical packaging systems described herein, is stable in intermediate conditions (e.g., 30° C./65% RH) for at least 6 months, at least 8 months, at least 10 months or at least 12 months. In certain instances, an oxygen sensitive drug, when stored in the pharmaceutical packaging systems described herein, is stable in intermediate conditions for at least 12 months. In further embodiments an oxygen sensitive drug, when stored in the pharmaceutical packaging systems described herein, is stable in accelerated conditions (e.g., 40° C./75% RH) for at least 4 months, at least 5 months, or at least 6 months. In certain instances, an oxygen sensitive drug, when stored in the pharmaceutical packaging systems described herein, is stable in accelerated conditions for at least 6 months.

The pharmaceutical packaging systems described herein are also suitable for pharmaceutical liquid compositions comprising an oxygen-sensitive excipient. Degradation of oxygen-sensitive excipients in a pharmaceutical composition can lead to a variety of effects ranging from discoloration of the composition, reduced performance or efficiency of the composition and/or harmful reactivity with the active pharmaceutical ingredient. Nonexclusive examples of oxygen-sensitive excipients that benefit from the pharmaceutical packaging systems described herein include polyethylene oxide (PEO) or polyethylene glycol (PEG) and polyoxyethylene akyl ethers.

Kits and Articles of Manufacture

For the pharmaceutical packaging systems described herein, kits and articles of manufacture are also described. Such kits comprise each of the components assembled together of the pharmaceutical packaging system and may optionally comprise an outer packaging surrounding the secondary packaging. A kit may also unit multiple pharmaceutical packaging systems for a particular drug to enable multi-dosing (e.g., a kit of one week of a daily dosed drug). Multiple pharmaceutical packaging systems in a kit may also contain different drugs for purposes such as drug combinations or rotations. A kit may comprise one or more additional components such as additional devices, desirable from a commercial and user standpoint for the pharmaceutical packaging systems. Non-limiting examples of such materials include, but not limited to, buffers, diluents, filters, needles, syringes; adaptors, waste receptacles, and/or labels listing contents and/or instructions for use, and package inserts with instructions for use associated with the pharmaceutical packaging system. A set of instructions will also typically be included.

A label can be on or associated with the secondary packaging. A label can be on a secondary packaging when letters, numbers or other characters forming the label are attached, molded or etched into the container itself; a label can be associated with a secondary packaging when it is present within a receptacle or carrier that also holds the primary packaging container, e.g., as a package insert. A label can be used to indicate that the contents are to be used for a specific therapeutic application. The label can also indicate directions for use of the contents, such as in the methods described herein.

The following examples further illustrate the invention but, of course, should not be construed as in any way limiting its scope.

EXAMPLE 1

Secondary Packaging Configurations and Analytical Equipment

Exemplary secondary packaging were developed and analyzed with respect to oxygen levels in the subsequent Examples 2 to 4. Different configurations allowed comparison of the materials' performance regarding oxygen barrier properties; oxygen absorber behavior and performance; and the kinetic and impact on the amount of oxygen inside the syringe. Furthermore, two systems were tested for oxygen removal in the secondary packaging: nitrogen flush before sealing the packaging or with use of an oxygen absorber.

Primary Packaging Container: Degassed water was filled into 1.25 mL glass syringes (Hypak™, Becton Dickinson & Co.) with an oxygen permeable tip cap. An OxyDot® oxygen sensor (visual indicator of oxygen levels) was stuck inside the syringe barrel before the filling.

Secondary Packaging: Materials for the secondary packaging included regular APET film which is without specific gas barrier properties; and multilayer films which included an EVOH layer as a gas barrier. Selected oxygen absorbers included an absorber in a sachet, absorber on a sticker and absorber embedded in the web film. The eight different tested configurations are described in the following table:

| Config-uration | Bottom Web | Top Web | Oxygen Removal |
|---|---|---|---|
| A | APET | Paper/Alu25 µm/PE | $N_2$ flush |
| C | PET/EVOH/PE | PET/Alu8 µm/PE | $N_2$ flush |
| D | PVC/PCTFE/EVOH | oPA/Alu45 µm/PVC | $N_2$ flush |
| E | APET | Paper/Alu20 µm/PE | $O_2$ absorber sachet 30 cc |
| E bis | APET | Paper/Alu20 µm/PE | $O_2$ absorber label 15 cc |
| F | PET/EVOH/PE | PET/Alu8 µm/PE | $O_2$ absorber label 15 cc |
| G | PET/EVOH/PE | Sealed Air OS | By top web 12 cc |
| O | PET/EVOH/PE | Paper/Alu20 µm/PE | $N_2$ flush |

APET: Amorphous Polyethylene terephthalate
PET: Polyethylene terephthalate
EVOH: Ethylene vinyl alcohol
PE: Polyethylene
PVC: Polyvinyl chloride
PCTFE: Polychlorotrifluoroethylene
Alu: Aluminum
Sealed Air OS: Oxygen Scavenger film delivered by Sealed Air Company Pouches were prepared with the two films (bottom web and top web) that encased the syringes and subsequently sealed. Four configurations were prepared with nitrogen flush (Configurations A, C, D and 0). The sealing of these pouches were performed in a glove box with a manual sealing clamp. Prior to sealing, an OxyDot® oxygen sensor was stuck inside the pouch. The other configurations contained a type of oxygen absorber (Configurations E, E bis, F and G). These were sealed in ambient air with an $O_2$ level of approximately 21%. Pouch dimensions were approximately 130 mm×90 mm and had a volume, with the syringe inside, of about 30 to 35 mL.

Analytical Equipment: The equipment used to measure the oxygen levels inside the pouches and the syringes included an oxygen analyzer that measured the oxygen level by reading the OxyDot® visual indicator (OxySense Analyzer) and ABL5 blood gas analyzer (Radiometer) which measured the oxygen level in the water of the syringe.

Storage: In the following Examples 2 to 4, the syringes in the secondary packaging were placed in a climatic chamber at 25° C./60% relative humidity (RH).

EXAMPLE 2

Oxygen Levels in Nitrogen Flushed Packaging

Oxygen in Pouch Environments

The following table depicts the oxygen levels for Configurations A, C, D and O.

| | Oxygen % in Configuration | | | | | | | | | |
|---|---|---|---|---|---|---|---|---|---|---|
| | Days | | | | | | | | | |
| Config | 0 | 14 | 30 | 60 | 90 | 120 | 150 | 180 | 210 | 360 |
| A | 0.06 | 0.44 | 0.93 | 1.83 | 2.62 | 3.34 | 3.98 | 4.6 | 5.18 | 7.91 |
| C | 0.16 | 0.22 | 0.33 | 0.48 | 0.65 | 0.8 | 0.97 | 1.14 | 1.24 | 1.91 |
| D | 0.27 | 0.33 | 0.47 | 0.53 | 0.57 | 0.55 | 0.6 | 0.65 | 0.65 | 0.79 |
| O | 0.83 | 0.96 | 1.09 | | | | 1.19 | 1.25 | 1.4 | 1.45 |

FIG. 4 is a graphical representation of the above table and depicts oxygen ingress in the nitrogen flushed pouches (Configurations A, C, D and O). Configurations A, C, D and O were all prepared with an aluminum foil top web. As the aluminum foil was very strong oxygen barrier properties, the top web impact on oxygen ingress is negligible. Thus, the graph allows essentially a direct comparison between the bottom web barrier properties.

At the beginning of the study (day=0) the oxygen levels in all configurations were about 0%, except for Configuration O with under 1%. Configuration A, comprised of the APET film without oxygen barrier properties, allowed steady ingress of oxygen. At the end of the study (day=360), the oxygen level of Configuration A was at about 8%. The other configurations C, D and O showed good barrier properties to oxygen permeation. However, these configurations still allowed oxygen ingress to a certain extent as oxygen levels inside the pouches increased by the study endpoint (e.g., 2% for C, 1% for D).

Oxygen in Syringe Environments

FIG. 5 shows the oxygen levels in the filled syringes of Configurations A, C and D. The filled syringes with degassed water had approximately 1% of residual oxygen at t0. According to FIG. 5, all the syringes' oxygen levels are close to zero % of oxygen after 1 month. It is contemplated that because the pouch environments of Configurations A, C and D had a lower oxygen levels than their syringes (See FIG. 4), the reduced oxygen level outside of the syringe promotes the egress of the residual oxygen inside the syringe as facilitated by the tip cap permeability according to Fick's law.

Nevertheless, a hysteresis phenomenon (lag effect) was observed between the oxygen level in the pouch environment and the oxygen level inside the syringe barrel. This is highlighted by the observation that after one year, syringes in the C and D configurations (placed in EVOH film) remained at zero % oxygen levels while the oxygen levels increased slightly in the respective pouches (2% for C, 1% for D). This effect was more prominent in configuration A, where the syringe in A (placed in regular APET film) remained at zero % oxygen for more than six months, after which the oxygen level started to increased after around the seventh month to 2% at the end of the study. In contrast, the oxygen level in the pouch environment of configuration A continually increased to 8% at the end of the study. FIG. 6 depicts this hysteresis phenomenon of the oxygen levels between the pouch and in the syringe for configuration A alone.

It is contemplated that the hysteresis phenomenon may be attributed to the oxygen sensor (OxyDot®) having intrinsic oxygen absorbing capacity as part of its sensing capability.

EXAMPLE 3

Oxygen Levels in Packaging with Oxygen Absorbers

Oxygen in Pouch Environments

Configurations E, E bis, F and G were examined with respect to oxygen levels inside the pouch and syringe environments. The study allowed comparison with the different materials for the secondary packaging and oxygen absorber types. FIG. 7 shows the oxygen levels in the pouch environment at storage of 360 days at 25° C./60% RH. As described in Example 1, configurations E, E bis, F and G were sealed in ambient air environment at 21% oxygen. Offsets at t0 are attributed to the time between the sealing of the pouch and the oxygen level measurement. After 2 to 3 days, the pouch environment of all the configurations (E, E bis, F and G) were at zero % oxygen. This indicates that the oxygen absorber absorbs rapidly the initial oxygen content within the pouch. FIG. 8 depicts in rapid absorption in more detail at in an 8-day scale graph. After 1 year, it was observed that configurations E and F are still at zero % of oxygen in the pouch environment (FIG. 7). For E bis, oxygen level started to increase after 6 months to a level of about 5% at the 1 year endpoint. Pouch G comprised of an oxygen absorbing top web film with a capacity of around 12 cc of $O_2$. However, the oxygen level in the pouch environment in configuration G started to increase after one month and the oxygen level was about 2% within the first 6 months, indicating that the oxygen absorbing capacity is not sufficient.

Regarding configurations E and F, the results indicate a ratio between the film barrier property (oxygen transfer rate) and oxygen absorber capacity can be manipulated to provide a zero % oxygen environment at the end of the study. Thus, a secondary packaging with a poor barrier (APET) and a large $O_2$ absorber capacity (30 cc), i.e., configuration E, and a secondary packaging, with a good barrier (EVOH) and a small $O_2$ absorber capacity (15 cc) can provide the same outcome (zero % pouch oxygen level).

Configuration E bis has the same secondary packaging materials but with a smaller capacity $O_2$ absorber (15 cc versus 30 cc for E). The results from FIG. 7 indicate that total capacity of the $O_2$ absorber was consumed at 6 months due to the poor barrier properties of the APET film. Oxygen ingress is then equivalent to configuration A, i.e., intake of 5% oxygen within 6 months. The results also showed that configuration G with the oxygen absorber embedded in the polymer base film had the slowest oxygen removal (3 days to zero % oxygen). Finally, the results showed that the oxygen absorption kinetics are very fast and can remove the total amount of oxygen in the pouch (approximately 6 to 7 cc of O2) in about 2 to 3 days.

It was also observed, unexpectedly, that the secondary packaging air pressure in some of the configurations achieved a lower than atmospheric pressure and created a vacuum-like effect.

Oxygen in Syringe Environments

FIG. 9 depicts the oxygen levels of syringe environments in configurations E, F and G. The filled syringes with degassed water had approximately 1% of residual oxygen at t0. After 1 month, the oxygen levels in the syringes of configurations E, F and G were at zero % of oxygen. The results suggest that the system tends to equilibrium the oxygen level outside (zero %) and inside the syringe. Interestingly however, the oxygen level in syringe G remains close to zero % oxygen despite the slight oxygen increase in the pouch (4% oxygen) after one year.

EXAMPLE 4

Sealing Effects of Secondary Packaging Configurations and Oxygen Levels

FIG. 10 illustrates a number of pouches from configurations E and G with defective sealing. As described previously, all pouches with oxygen absorbers were sealed at 21% oxygen level. The results from FIG. 10 show that most of these samples reached zero % oxygen and went back up to 21% at different points of time, depending on the leak rate of each sample or the rupture of the sealing cord after a certain time. Despite the over-sizing of the oxygen absorber (30 cc capacity in E compared to 7 cc of pure oxygen in the pouch volume), the oxygen level in the pouch can rise back to 21% very quickly if the package is leaking. The large number of defective pouches from configuration E suggests that some materials have better sealing properties than others and is a consideration for secondary packaging.

EXAMPLE 5

Oxygen Levels of Syringes Filled in Ambient Conditions (~21% $O_2$) in Blister

Packaging with Oxygen Absorbers

This study assessed the oxygen level and extraction kinetic from a syringe filled in ambient conditions (concentration of $O_2$ is ~21%). Three different blister configurations (n=10, per configuration) containing oxygen absorbers at a volume about 32 cc were prepared with the following materials at ambient conditions (~21% $O_2$):

| Configuration | Bottom Web | Top Web | Oxygen Absorber |
|---|---|---|---|
| 1 (♦) | PET/EVOH/PE 500 μm | Paper/Alu9 μm/PE | Sachet 30 cc |
| 2 (■) | PET/EVOH/PET 457 μm | Paper/PET/Alu20 μm | Canister 30 cc |
| 3 (▲) | PET/EVOH/LDPE 457 μm | Paper/Alu9 μm/PE | Canister 30 cc |

1.25 mL glass syringes (Hypak™, Becton Dickinson & Co.) with an oxygen permeable tip cap. were filled with purified water (not degassed) and subsequently placed into one of the above blister packaging. Thus, the water contained 8 ppm of initial oxygen levels (equilibrium with air at 21% oxygen). An OxyDot® oxygen sensor (visual indicator of oxygen levels) was stuck inside the syringe barrel before the filling. Oxygen levels were assessed in the blister packaging and in the syringe according to the method described in Example 1.

Oxygen in Blister Environments

For all three configurations, the oxygen level is zero in the blister packaging after one day and remains at zero until the end of the study (360 days) (FIG. 11). This indicates that the kinetics of the oxygen absorption has a much faster rate than the oxygen permeation flow through the blister. In FIG. 11, the oxygen concentration at T0 (time zero) should be 21% but the time delay between sample manufacturing and the measurement (span of a few hours) is sufficient to get low concentrations on the first point of measurement.

Oxygen in Syringe Environments

For a syringe filled in ambient conditions (oxygen at 21%) and placed in the blister packaging with oxygen absorber, the oxygen level in the syringe decreases to 5% within six months, and less than 2% around one year for all three blister configurations (FIG. 12). The trend line in FIG. 12 appears to follow an exponential curve.

The study showed that the oxygen extraction flow from inside the syringe is a relatively slow process: it takes about six months to decrease the oxygen levels around 5%, and one year for oxygen levels around 2%. This slow kinetic indicates that syringes filled in ambient conditions will expose the syringes' contents to about six months of oxygen exposure, thus likely having a high risk of oxidation/degradation. Although the packaging eventually reduces the oxygen levels in the syringe to under 2% in about a year, it is recommended to fill the syringe in inert (i.e., nitrogen) conditions to prevent possibility of degradation.

EXAMPLE 6

Oxygen Levels in the Syringe at Various Fill and Packaging Conditions

FIG. 13 summarizes oxygen levels in syringes of various fill and packaging conditions over the course of a year. For a syringe filled in inert conditions (degassed, $N_2$ flushed) with ~1% $O_2$ level and placed in ambient air storage (no, secondary packaging), the oxygen levels eventually increased to 21% in approximately one year (▲). For a syringe filled in inert conditions (degassed, $N_2$ flushed) with ~1% $O_2$ level and placed in oxygen barrier packaging with an absorber, the oxygen levels decrease to zero in about one month and remain there after about one year (♦). A syringe filled in ambient conditions ($O_2$ level ~21%) and placed in oxygen barrier packaging with an absorber, the oxygen levels decrease to about 1% after one year (■).

EXAMPLE 7

Accelerated Stability Studies of a Morphine Formulation in Primary and Secondary Packaging without Oxygen Absorber 2 mg/mL and 10 mg/mL morphine formulations were prepared according to the following table.

| Material | 2 mg/mL | 10 mg/mL |
| --- | --- | --- |
| Morphine sulfate pentahydrate | 2.00 mg | 10.00 mg |
| Sodium chloride | 8.40 mg | 7.50 mg |
| Sodium citrate dihydrate | 2.30 mg | 3.45 mg |
| Citric Acid monohydrate | 0.74 mg | 1.11 mg |
| Disodium edetate dihydrate | 0.111 mg | 0.111 mg |
| Calcium chloride dihydrate | 0.053 mg | 0.053 mg |
| Water for injection | s.q.f 1 mL | s.q.f 1 mL |

The 2 mg/mL and 10 mg/mL morphine formulations were evaluated under ICH accelerated conditions at 40° C./75% RH for 6 months in 1.25 mL glass syringes (Hypak™) with an oxygen permeable stopper. The syringes containing the morphine formulations were placed in a secondary blister packaging of PET (polyethylene terephthalate) material with a paper lid backing.

Results of the stability assay after 6 months storage at 40° C./75% RH revealed that morphine content in stayed within specification parameters (NMT ±10% change) for both concentrations. The assay values stayed stable in the 2 mg/mL formulation while the assay values for morphine decreased slightly in the 10 mg/mL formulation but remained within specification. Similarly, total impurities level increased regularly over time but stay below the specification (NMT 1.5%) for both strengths. pH values also remained stable over the 6 month storage period.

With respect to individual impurities, pseudomorphine appeared after 1 month storage period and increased regularly over the storage period in both the 2 mg/mL and 10 mg/mL morphine formulations. At the end of 6 months storage, this impurity passed the specification limit (NMT 0.2%). The following table describes the pseudomorphine concentration over time in the 2 mg/mL morphine formulation:

| | 2 mg/mL Morphine in Oxygen Barrier Packaging - Pseudomorphine Content | | | | |
| --- | --- | --- | --- | --- | --- |
| | T0 | T1 Month | T2 Months | T3 Months | T6 Months |
| Batch 1 | 0 | 0.05 | 0.05 | 0.1 | 0.21 |
| Batch 2 | 0 | 0.05 | 0.06 | 0.11 | 0.23 |
| Batch 3 | 0 | 0.06 | 0.06 | 0.11 | 0.24 |

FIG. 14 depicts the presence of pseudomorphine over time in the 2 mg/mL formulation of three different batches. The pseudomorphine increase was at a greater rate in the 10 mg/mL formulation and reached the specification limit earlier (data not shown).

EXAMPLE 8

Accelerated Stability Studies of a Morphine Formulation in Primary and Secondary Packaging with Oxygen Absorber In order to improve the stability and shelf life of the morphine formulation of Example 7, a secondary packaging with an oxygen absorber was developed.

The alternative blister packaging included a thermoformed transparent shell made of a multilayer plastic film including PET and EVOH (Ethylene vinyl alcohol) (bottom web), and a heat sealed lidding material made of paper, PET and aluminum foil (top web). The EVOH layer of the bottom web presents a very low permeability to oxygen molecules and the aluminum foil is impermeable to any gas. Thus, this blister packaging restricts the atmospheric oxygen re-entry into the secondary packaging. An oxygen absorber (30 cc capacity) was placed inside the blister. This absorber included an iron powder formula filled in a canister made of HDPE plastic and functioned to absorb any oxygen present in the secondary packaging. The primary packaging container, i.e., syringe, containing the morphine formulation was then placed in this alternative blister packaging.

Accelerated conditions at 40° C./75% RH for 6 months were assessed similarly to the previous example. For both strengths, the morphine content remained stable over time and the results were compliant with the specification (90-110%). However, with the secondary packaging system with an oxygen absorber configuration, the impurity profile, and more specifically the pseudomorphine impurity, was considerably improved. For all batches of the both strengths, the highest result of total impurities content were very low and stayed very far below the specification limit (NMT 1.5%). The pseudomorphine content was very low and even below the limit of quantification. Results of pseudomorphine content over the 6-month storage period in accelerated conditions are presented in the following tables:

| 2 mg/mL Morphine in Oxygen Barrier Packaging - Pseudomorphine Content | | | | | |
|---|---|---|---|---|---|
| | T0 | T1 Month | T2 Months | T3 Months | T6 Months |
| Batch 1 | ND | 0.05 | 0.03 | 0.04 | 0.04 |
| Batch 2 | ND | 0.05 | 0.03 | 0.04 | 0.03 |
| Batch 3 | ND | 0.04 | 0.01 | 0.02 | 0.01 |

| 10 mg/mL Morphine in Oxygen Barrier Packaging - Pseudomorphine Content | | | | | |
|---|---|---|---|---|---|
| | T0 | T1 Month | T2 Months | T3 Months | T6 Months |
| Batch 1 | 0.02 | 0.02 | 0.03 | 0.03 | 0.03 |
| Batch 2 | 0.02 | 0.02 | 0.02 | 0.03 | 0.02 |
| Batch 3 | 0.02 | 0.02 | 0.03 | 0.02 | 0.03 |

As shown above, the pseudomorphine content also stayed far below the specification limit (NMT 0.2%). The data in the example showed that the stability results obtained on the batches packaged with the secondary packaging system with an oxygen absorber show that the combination of the formulation with the buffer and chelating systems, the manufacturing process under nitrogen and the oxygen barrier packaging with an oxygen absorber ensure a good preservation of the morphine formulation against oxidation reactions.

Comparison of Morphine Formulations in Oxygen Barrier Packaging with Standard Packaging In another study, the stability of 2 mg/mL morphine formulation was examined in standard packaging (i.e., without oxygen barrier secondary packaging and/or oxygen absorber) and in oxygen barrier packaging (i.e., with oxygen barrier secondary packaging and oxygen absorber) at ambient (25° C./60% RH) and accelerated conditions (40° C./75% RH). The following tables show that in both ambient and accelerated conditions, the pseudomorphine content in the morphine formulations with oxygen barrier packaging was low and under the specification limits whereas the morphine formulations with standard packaging had unacceptable levels (0.2% or higher) of pseudomorphine:

| 2 mg/mL Morphine in Oxygen Barrier Packaging - Pseudomorphine Content Storage - 25° C./60% RH | | | | | | | |
|---|---|---|---|---|---|---|---|
| | T0 | T3 Months | T6 Months | T9 Months | T12 Months | T18 Months | T24 Months |
| Standard packaging | 0 | 0.040 | 0.060 | 0.080 | 0.110 | 0.210 | 0.300 |
| O₂ Barrier Packaging | 0 | 0.020 | 0.024 | 0.030 | 0.033 | N/A | 0.032 |

| 2 mg/mL Morphine in Oxygen Barrier Packaging - Pseudomorphine Content Storage - 40° C./75% RH | | | | | |
|---|---|---|---|---|---|
| | T0 | T1 Month | T2 Months | T3 Months | T6 Months |
| Standard packaging | 0.010 | 0.050 | 0.090 | 0.100 | 0.200 |
| O₂ Barrier Packaging | 0.010 | 0.040 | 0.020 | 0.030 | 0.030 |

FIG. 15 is a graphical representation of the results in the previous tables. FIG. 15 (top) shows storage of 2 mg/mL morphine (MPH) formulations in standard and oxygen barrier packaging at ambient conditions (25° C./60% RH) for 24 months. The graph shows that the 2 mg/mL morphine formulation in standard packaging, when stored at ambient conditions attained unacceptable pseudomorphine impurity levels at around 18 months. FIG. 15 (bottom) storage of 2 mg/mL morphine formulations in standard and oxygen barrier packaging at accelerated conditions (40° C./75% RH) for six months. At the end of the six month period in accelerated conditions, the morphine formulations in standard packaging reached the specification limit for pseudomorphine. The morphine formulations in oxygen barrier packaging stored in both ambient and accelerated conditions were stable and had pseudomorphine levels well below the specification limits.

EXAMPLE 9

Stability Comparison of Morphine Formulations from Example 7 in Oxygen Barrier Packaging with Marketed Morphine Formulation Products of Equal Strengths 2 mg/mL, 5 mg/mL and 10 mg/mL morphine formulations were prepared according to Example 7 and filled into 1.25 mL glass syringes (Hypak™) with a stopper and placed into the secondary packaging system with an oxygen absorber as described in Example 8. The stability was compared with marketed morphine formulation products of equal strengths. The testing conditions and results are summarized in the following table:

| | | Product Name | | | | | |
|---|---|---|---|---|---|---|---|
| | | Morphine Product on Market 2 mg/mL | Example 7 Morphine formulation with O2 barrier packaging 2 mg/mL | Morphine Product on Market 5 mg/mL | Example 7 Morphine formulation with O2 barrier packaging 5 mg/mL | Morphine Product on Market 10 mg/mL | Example 7 Morphine formulation with O2 barrier packaging 10 mg/mL |
| | | | | Test time point & condition | | | |
| | | Tested at 17 mos. Ambient conditions | Tested at 6 mos. at 40° C./ 75% RH | Tested at 2 mos. After expiry Ambient conditions | Tested at 6 mos. at 40° C./ 75% RH | Tested at 13 mos. Ambient conditions | Tested at 6 mos. at 40° C./ 75% RH |
| | | | | Expiry date | | | |
| Analytical Tests | | 24 mos at 20° C.-25° C. | 24 mos at 20° C.-25° C. (proposed) | 24 mos at 20° C.-25° C. | 24 mos at 20° C.-25° C. (proposed) | 24 mos at 20° C.-25° C. | 24 mos at 20° C.-25° C. (proposed) |
| Assay of Morphine (%) | 90%-110% | 101% | 101% | 101% | 100% | 104% | 100% |
| Total Impurities (%) | NMT 1.0% | 1.7% | 0.0% | 0.7% | 0.1% | 1.1% | 0.0% |
| Codeine Impurity | NMT 0.2% | 0.06% | 0.05% | 0.06% | 0.04% | 0.07% | 0.05% |
| Pseudomorphine impurity | NMT 0.2% | ND | 0.04% | 0.23% | 0.03% | ND | 0.03% |
| Oripavine impurity | NMT 0.2% | ND | ND | ND | ND | ND | ND |
| 10-hydroxymorphine impurity | NMT 0.2% | 0.15% | 0.04% | 0.04% | 0.06% | 0.08% | 0.03% |
| Morphine-N-oxide | NMT 0.2% | ND | ND | ND | 0.05% | ND | ND |
| Normorphine impurity | NMT 0.2% | ND | ND | ND | ND | ND | ND |
| Morphinone impurity | NMT 0.2% | ND | ND | 0.07% | ND | ND | ND |
| Apomorphine impurity | NMT 0.2% | ND | — | ND | — | ND | ND |
| Unknown impurity | NMT 0.2% | RRT (%) 0.096 (0.38%) 0.144 (0.12%) 0.165 (0.38%) 0.182 (0.08%) 0.213 (0.05%) 0.284 (0.15%) 0.391 (0.24%) 0.434 (0.08%) | RRT (%) 0.16 (0.02%) | RRT (%) 0.120 (0.21%) 1.102 (0.06%) | RRT (%) 0.16 (0.03%) | RRT (%) 0.097 (0.10%) 0.144 (0.15%) 0.166 (0.19%) 0.185 (0.10%) 0.284 (0.16%) 0.394 (0.22%) | RRT (%) 0.16 (0.02%) |

As shown above, the morphine formulations of Example 7 in secondary packaging system with an oxygen absorber had much better stability than the marketed morphine products of comparable strengths even when the marketed morphine products were stored at ambient conditions while the morphine formulations of Example 7 were stored in accelerated (40° C./75% RH) conditions. The stability assay shows that all of the marketed morphine products were out of specification limits for either total and/or a particular impurity while the morphine formulations of Example 7 were completely within specification. The marketed morphine product at 2 mg/mL presented a high level of total impurities (1.7%) and was out of specification (according to ICH Q3B guidance) for two unknown impurities; other unknown impurities were found significantly greater than 0.1%. The marketed morphine product at 5 mg/mL showed unacceptable pseudomorphine and unknown impurity levels. Finally, the marketed morphine product at 10 mg/mL, analyzed at about half of its shelf life had a high total impurity level and up to 6 unknown impurities, 4 of which being very close or that could be rounded to 0.2%; this indicates that this product is unlikely to meet stability acceptance criteria after two years. The results in this example demonstrate the increased purity and stability of exemplary morphine formulations described herein with the secondary packaging system with the oxygen absorber.

EXAMPLE 10

Additional Stability Studies with Various Oxygen Sensitive Drugs in Standard and Oxygen Barrier Packaging Additional stability studies were performed for hydromorphone and promethazine formulation similar to the morphine standard vs. oxygen barrier packaging study in Example 8.

Hydromorphone

The stability of 1 mg/mL and 10 mg/mL hydromorphone formulations were examined in standard packaging (i.e., without oxygen barrier secondary packaging and/or oxygen absorber) and in oxygen barrier packaging (i.e., with oxygen barrier secondary packaging and oxygen absorber) at ambient (25° C./60% RH) for 24 months and accelerated conditions (40° C./75% RH) for six months.

At ambient conditions, no significant difference in the impurity content was observed for the 1 mg/mL hydromorphone formulations in either standard or oxygen barrier packaging. However, at accelerated conditions, both 1 mg/mL and 10 mg/mL exhibit unknown impurity at RRT 0.72 which exceeded or was close to the specification limits:

| | 1 mg/mL Hydromorphone in Oxygen Barrier Packaging - RRT 0.72 Impurity Content Storage - 40° C./75% RH | | | | |
|---|---|---|---|---|---|
| | T0 | T1 Month | T2 Months | T3 Months | T6 Months |
| Standard packaging | 0 | N/A | N/A | 0.090 | 0.240 |
| O$_2$ Barrier Packaging | 0 | N/A | N/A | 0.080 | 0.070 |

| | 10 mg/mL Hydromorphone in Oxygen Barrier Packaging - Pseudomorphine Content Storage - 40° C./75% RH | | | | |
|---|---|---|---|---|---|
| | T0 | T1 Month | T2 Months | T3 Months | T6 Months |
| Standard packaging | 0 | N/A | N/A | 0.080 | 0.190 |
| O$_2$ Barrier Packaging | 0 | N/A | N/A | 0.040 | 0.030 |

FIG. 16 is a graphical representation of the results in the previous table. FIG. 16 (top) shows storage of 1 mg/mL hydromorphone (HYD) formulations in standard and oxygen barrier packaging at accelerated conditions (40° C./75% RH) for six months. The graph shows that the 1 mg/mL hydromorphone formulation in standard packaging had an unacceptable unknown impurity (RRT 0.72) at the end of the six month storage period. FIG. 16 (bottom) storage of 10 mg/mL hydromorphone formulations in standard and oxygen barrier packaging at accelerated conditions (40° C./75% RH) for six months. At the end of the six month period in accelerated conditions, the hydromorphone formulations in standard packaging was very close to the specification limit for the unknown impurity (RRT 0.72). The 1 mg/mL and 10 mg/mL hydromorphone formulations in oxygen barrier packaging were stable with impurity levels stable and below the specification limits.

Promethazine

The stability of 25 mg/mL promethazine formulations were examined in standard packaging (i.e., without oxygen barrier secondary packaging and/or oxygen absorber) and in oxygen barrier packaging (i.e., with oxygen barrier secondary packaging and oxygen absorber) at ambient (25° C./60% RH) for 24 months and accelerated conditions (40° C./75% RH) for six months.

The following tables show that in both ambient and accelerated conditions, the sulfoxide impurity content in the promethazine formulations with oxygen barrier packaging were under the specification limits whereas the promethazine formulations with standard packaging quickly had unacceptable levels (0.2% or higher) of the sulfoxide impurity:

| | 25 mg/mL Promethazine in Oxygen Barrier Packaging - Sulfoxide Content Storage - 25° C./60% RH | | | | | | |
|---|---|---|---|---|---|---|---|
| | T0 | T3 Months | T6 Months | T9 Months | T12 Months | T18 Months | T24 Months |
| Standard packaging | 0.17 | 0.67 | 1.21 | N/A | 1.55 | 0.21 | 0.30 |
| O$_2$ Barrier Packaging | 0.12 | 0.17 | 0.17 | N/A | 0.13 | N/A | 0.032 |

| | 25 mg/mL Promethazine in Oxygen Barrier Packaging - Sulfoxide Content Storage - 40° C./75% RH | | | | |
|---|---|---|---|---|---|
| | T0 | T1 Month | T2 Months | T3 Months | T6 Months |
| Standard packaging | 0.173 | 0.451 | N/A | 0.854 | 1.46 |
| O$_2$ Barrier Packaging | 0.12 | 0.177 | 0.114 | 0.104 | 0.12 |

FIG. 17 is a graphical representation of the results in the previous table. FIG. 17 (top) shows storage of 25 mg/mL promethazine (PRZ) formulations in standard and oxygen barrier packaging at ambient conditions (25° C./60% RH) for twelve months. The graph shows that the promethazine formulation in standard packaging had an unacceptable levels of sulfoxide by the three-month assay point which continued to increase to the end of the storage period. The promethazine formulation in oxygen barrier packaging had sulfoxide impurity levels under the specification limits. FIG. 17 (bottom) storage of 25 mg/mL promethazine formulations in standard and oxygen barrier packaging at accelerated conditions (40° C./75% RH) for six months. At the one-month assay point, the promethazine formulations in standard packaging already exceeded the specification limit for sulfoxide. The promethazine formulations in oxygen barrier packaging were stable with sulfoxide impurity levels stable and below the specification limits.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:
1. A pharmaceutical product comprising:
   (i) a container filled under inert conditions with an injectable oxygen-sensitive drug, wherein the syringe has an oxygen permeable tip cap,
   (ii) a hermetically sealed oxygen barrier blister packaging which houses the syringe, wherein the blister packaging comprises a multilayer bottom web comprising ethylene vinyl alcohol (EVOH) and a multilayer top web lid comprising aluminum foil or EVOH; wherein the multilayer bottom web and multilayer top web lid are comprised of different materials; and
   (iii) an oxygen absorber inside the blister packaging, wherein the oxygen absorber reduces the oxygen level present from the time of packaging assembly to about zero percent in about one to three days in the blister packaging and in about one to three months in the syringe, and the oxygen levels in the blister packaging and in the syringe remain at about zero percent for at least one year after the initial reduction in oxygen levels.

2. The pharmaceutical product of claim 1, wherein the syringe is plastic or glass.

3. The pharmaceutical product of claim 1, wherein the blister packaging is an aluminum-based cold formed blister, or a molded blister.

4. The pharmaceutical product of claim 1, wherein the oxygen absorber is a canister.

5. The pharmaceutical product of claim 1, wherein the oxygen absorber has a capacity to absorb about 30 cc oxygen at 1 atm.

6. The pharmaceutical product of claim 1, wherein the oxygen absorber is iron-based.

7. The pharmaceutical product of claim 1, wherein the oxygen absorber reduces the oxygen level in the blister packaging from the time of packaging assembly to about zero percent at about one day.

8. The pharmaceutical product of claim 1, wherein the oxygen absorber reduces the oxygen level in the syringe from the time of packaging assembly to about zero percent at about one month.

9. The pharmaceutical product of claim 1, wherein the oxygen level remains at about zero percent in the syringe and the blister packaging for at least three years.

10. The pharmaceutical product of claim 1, wherein the blister packaging is a thermoformed blister.

11. The pharmaceutical product of claim 1, wherein the oxygen absorber is selected from reduced iron compounds, catechol, ascorbic acid and analogs thereof, metal ligands, unsaturated hydrocarbons and polyamides.

12. The pharmaceutical product of claim 1, wherein the oxygen absorber is a sachet, pouch, canister, capsule, label, sticker, strip, patch, cartridge or container.

13. The pharmaceutical product of claim 1, wherein the injectable oxygen-sensitive drug is selected from morphine, hydromorphone, promethazine, dopamine, epinephrine, norepinephrine, esterified estrogen, ephedrine, pseudoephedrine, acetaminophen, ibuprofen, danofloxacin, erythromycin, penicillin, cyclosporine, methyldopa, cetirizine, diltiazem, verapamil, mexiletine, chlorothiazide, carbamazepine, selegiline, oxybutynin, vitamin A, vitamin B, vitamin C, L-cysteine and L-tryptophan.

14. The pharmaceutical product of claim 1, wherein the multilayer bottom web further comprises polyethylene terephthalate (PET).

15. The pharmaceutical product of claim 1, wherein the multilayer top web lid comprises aluminum foil and paper.

16. A pharmaceutical product comprising:
   (i) a syringe filled under inert conditions with morphine, wherein the syringe has an oxygen permeable tip cap,
   (ii) a hermetically sealed oxygen barrier blister packaging which houses the syringe, wherein the blister packaging comprises a multilayer bottom web comprising ethylene vinyl alcohol (EVOH) and a multilayer top web lid comprising aluminum foil or EVOH, wherein the multilayer bottom web and multilayer top web lid are comprised of different materials; and
   (iii) an oxygen absorber inside the blister packaging, wherein the oxygen absorber reduces the oxygen level present from the time of packaging assembly to about zero percent in about one to three days in the blister packaging and in about one to three months in the syringe, and the oxygen levels in the blister packaging and in the syringe remain at about zero percent for at least one year after the initial reduction in oxygen levels.

17. The pharmaceutical product of claim 16, wherein the multilayer bottom web further comprises polyethylene terephthalate (PET).

18. The pharmaceutical product of claim 16, wherein the multilayer top web lid comprises aluminum foil and paper.

19. A pharmaceutical product comprising:
(i) a syringe filled under inert conditions with hydromorphone, wherein the syringe has an oxygen permeable tip cap,
(ii) a hermetically sealed oxygen barrier blister packaging which houses the container, wherein the blister packaging comprises a multilayer bottom web comprising ethylene vinyl alcohol (EVOH) and a multilayer top web lid comprising aluminum foil or EVOH, wherein the multilayer bottom web and multilayer top web are comprised of different materials; and
(iii) an oxygen absorber inside the blister packaging, wherein the oxygen absorber reduces the oxygen level present from the time of packaging assembly to about zero percent in about one to three days in the blister packaging and in about one to three months in the syringe, and the oxygen levels in the blister packaging and in the syringe remain at about zero percent for at least one year after the initial reduction in oxygen levels.

20. The pharmaceutical product of claim 19, wherein the multilayer bottom web further comprises polyethylene terephthalate (PET).

21. The pharmaceutical product of claim 19, wherein the multilayer top web lid comprises aluminum foil and paper.

* * * * *